United States Patent
Lagrange

(10) Patent No.: US 7,427,301 B2
(45) Date of Patent: Sep. 23, 2008

(54) COMPOSITION COMPRISING AT LEAST ONE SUBSTITUTED CARBOCYANIN DERIVATIVE, PROCESS FOR TREATING KERATIN FIBERS USING IT, DEVICE THEREFOR AND USE THEREOF

(75) Inventor: Alain Lagrange, Coupvray (FR)

(73) Assignee: L'Oréal S.A., Paris (FR)

( * ) Notice: Subject to any disclaimer, the term of this patent is extended or adjusted under 35 U.S.C. 154(b) by 344 days.

(21) Appl. No.: 11/223,962

(22) Filed: Sep. 13, 2005

(65) Prior Publication Data

US 2006/0075582 A1    Apr. 13, 2006

Related U.S. Application Data

(60) Provisional application No. 60/616,526, filed on Oct. 7, 2004.

(30) Foreign Application Priority Data

Sep. 13, 2004    (FR) .................................. 04 09694

(51) Int. Cl.
*A61Q 5/10* (2006.01)
(52) U.S. Cl. .................. 8/405; 8/406; 8/407; 8/409; 8/416; 8/431; 8/565; 8/571; 8/575; 8/576
(58) Field of Classification Search ............ 8/405, 8/406, 407, 409, 416, 431, 565, 571, 575, 8/576
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 2,798,053 A | 7/1957 | Brown | |
| 2,923,692 A | 2/1960 | Ackerman et al. | |
| 3,666,464 A | 5/1972 | Keller et al. | |
| 3,679,427 A | 7/1972 | Lincoln et al. | |
| 3,821,233 A | 6/1974 | Lincoln et al. | |
| 3,864,644 A * | 2/1975 | Lincoln et al. | 372/53 |
| 3,904,637 A | 9/1975 | Lincoln et al. | |
| 3,915,921 A | 10/1975 | Schlatzer, Jr. | |
| 4,011,086 A | 3/1977 | Simson | |
| 4,237,243 A | 12/1980 | Quack et al. | |
| 4,309,551 A | 1/1982 | Schönberger et al. | |
| 4,509,949 A | 4/1985 | Huang et al. | |
| 4,823,985 A | 4/1989 | Grollier et al. | |
| 5,089,578 A | 2/1992 | Valint et al. | |
| 5,474,578 A | 12/1995 | Chan et al. | |
| 5,708,151 A | 1/1998 | Möckli | |
| 5,733,343 A | 3/1998 | Möckli | |
| 5,734,058 A | 3/1998 | Lee | |
| 5,792,221 A | 8/1998 | Lagrange et al. | |
| 5,830,446 A | 11/1998 | Berthiaume et al. | |
| 5,914,373 A | 6/1999 | Glancy et al. | |
| 5,981,747 A | 11/1999 | Mujumdar et al. | |
| 5,986,093 A | 11/1999 | Mujumdar et al. | |
| 6,120,780 A | 9/2000 | Dupuis et al. | |
| 6,133,445 A * | 10/2000 | Waggoner et al. | 546/36 |
| 6,228,129 B1 | 5/2001 | De La Mettrie et al. | |
| 6,686,145 B1 | 2/2004 | Waggoner et al. | |

(Continued)

FOREIGN PATENT DOCUMENTS

| | | |
|---|---|---|
| DE | 3829870 A1 | 4/1989 |
| DE | 19732016 A1 | 1/1999 |
| EP | 0 121 326 A2 | 10/1984 |
| EP | 0 173 109 B1 | 10/1989 |
| EP | 0 395 282 B1 | 3/1995 |
| EP | 0 503 853 B1 | 5/1996 |

(Continued)

OTHER PUBLICATIONS

STIC Search Report dated Jun. 6, 2007.*

(Continued)

*Primary Examiner*—Eisa B Elhilo
(74) *Attorney, Agent, or Firm*—Finnegan, Henderson, Farabow, Garrett & Dunner LLP

(57) ABSTRACT

Disclosed is a composition for dyeing keratin fibers, for example, human keratin fibers, comprising, in a cosmetically acceptable medium, at least one direct dye of the following formulae:

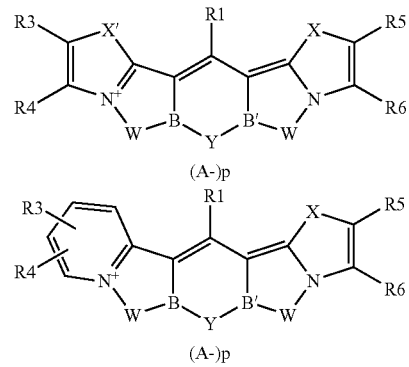

Also disclosed is a process for treating keratin fibers, for example, human keratin fibers, using the above composition, and also to a multi-compartment device comprising at least one composition as defined above.

37 Claims, No Drawings

U.S. PATENT DOCUMENTS

| | | | |
|---|---|---|---|
| 6,783,559 | B2 | 8/2004 | De La Mettrie et al. |
| 6,822,039 | B1 | 11/2004 | Monfreux-Gaillard et al. |
| 6,878,169 | B2 | 4/2005 | Matsunaga |
| 2002/0010967 | A1 | 1/2002 | De La Mettrie et al. |
| 2003/0009833 | A9 | 1/2003 | De La Mettrie et al. |
| 2003/0124079 | A1 | 7/2003 | Mougin et al. |
| 2003/0224391 | A1 | 12/2003 | Waggoner et al. |
| 2004/0078906 | A1 | 4/2004 | Plos et al. |
| 2004/0088798 | A1 | 5/2004 | Lang |
| 2004/0205901 | A1 | 10/2004 | Cottard et al. |
| 2005/0028301 | A1 | 2/2005 | Pastore |
| 2005/0144741 | A1 | 7/2005 | Lang et al. |
| 2006/0010617 | A1 | 1/2006 | Gourlaouen et al. |
| 2006/0117497 | A1 | 6/2006 | Lang et al. |
| 2007/0039107 | A1 | 2/2007 | Lang et al. |

FOREIGN PATENT DOCUMENTS

| | | |
|---|---|---|
| EP | 0 747 448 A2 | 12/1996 |
| EP | 0 750 899 A2 | 1/1997 |
| EP | 0 815 828 B1 | 2/1999 |
| EP | 1 133 978 A2 | 9/2001 |
| EP | 1 166 753 A2 | 1/2002 |
| EP | 1 166 757 A2 | 1/2002 |
| EP | 1 170 001 A2 | 1/2002 |
| EP | 0 714 954 B1 | 9/2002 |
| EP | 1 352 632 A1 | 10/2003 |
| EP | 1 415 643 A1 | 5/2004 |
| EP | 1634575 | 3/2006 |
| EP | 1652553 | 5/2006 |
| EP | 1652554 | 5/2006 |
| FR | 1573139 | 5/1969 |
| FR | 2 416 723 A1 | 9/1979 |
| FR | 2 586 913 A1 | 3/1987 |
| FR | 2 692 572 A1 | 12/1993 |
| FR | 2 741 261 | 5/1997 |
| FR | 2 811 993 A1 | 1/2002 |
| FR | 2 820 032 A1 | 8/2002 |
| FR | 2 875 130 | 3/2006 |
| FR | 2 875 131 | 3/2006 |
| FR | 2 875 132 | 3/2006 |
| GB | 1 529 807 | 10/1978 |
| JP | 55-12407 | 4/1980 |
| JP | A 2000-086472 | 3/2000 |
| JP | T 2000-507986 | 6/2000 |
| JP | T 2000-507987 | 6/2000 |
| JP | A-2001-261534 | 9/2001 |
| JP | T 2002-508428 | 3/2002 |
| JP | T 2003-528054 | 9/2003 |
| JP | A 2004-210778 | 7/2004 |
| JP | 2006-083170 | 3/2006 |
| WO | WO 95/01772 A1 | 1/1995 |
| WO | WO 95/15144 A1 | 6/1995 |
| WO | WO 97/17471 | 5/1997 |
| WO | WO 99/13849 | 3/1999 |
| WO | WO 99/31181 | 6/1999 |
| WO | WO 00/31154 A1 | 6/2000 |
| WO | WO 00/68282 A1 | 11/2000 |
| WO | WO 03/028685 A1 | 4/2003 |

OTHER PUBLICATIONS

Eaves, J. et al., "An MNDO study of dipyridopyrazinium and relation cations: instability of certain fused heteroaromic dications with two bridgehead nitrogens" *Can. J. Chem.* 64:1711-13 (1986).

Fonnum, G. et al., "Associative thickeners. Part I: Synthesis, rheology and aggregation behavior," *Colloid Polym. Sci.* 271(4):380-89 (1993).

Morishima, Y., "Self-assembling amphiphilic polyelectrolytes and their nanostructures," *Chinese J. Polymer Science* 18(40):323-36 (2000).

Noda, T. et al., "Micelle formation of random copolymers of sodium 2-(acrylamido)-2-methylpropanesulfonate and a nonionic surfactant macromonomer in water as studied by fluorescence and dynamic light scattering," *Macromolecules* 33(10):3694-3704 (2000).

Noda, T. et al., "Solution properties of micelle networks formed by nonionic surfactant moieties covalently bound to a polyelectrolyte: salt effects on rheological behavior," *Langmuir* 16(12):5324-32 (2000).

Noda, T. et al., "Stimuli responsive amphiphilic copolymers of sodium 2-(acrylamido)-2-methylpropanesulfonate and associative macromonomers," *Polymers Preprints* 40(2):220-221 (1999).

Tredwell, C. et al., "Picosecond time resolved fluorescence lifetimes of the polymethine and related dyes," *Chem. Phys.* 43(3):307-16 (1979).

Zviak, C., *The Science of Hair Care*, Masson, Paris, pp. 215, 278 (1988).

Yarmolyuk, S.M. "Interaction of Cyanine Dyes with Nucleic Acids: Investigation of Cyanine Dyes as Fluorescent Probes for the Nucleic Acids: Investigation of Cyanine Dyes as Fluorescent Probes for the Nucleic Acids Detection," *Biopolimeriy I Kletka*, 15 (4):328-336 (1999).

Romanov, N.N. et al., "Cyanine Dyes with three cyclic groupings of dihydrooxazino- and dihydrothiazinobenzothiasolium salts," Dopovidi Akademii Nauk Ukrains'Koi RSR, Seriya B: Geologichni, Khimichni Ta Biologichni Nauki, (7), 622-4 (1976).

English Language Abstract of JP-A-2001-261534 (2001).

Porter, M.R. "Handbook of Surfactants," Blackie & Son, LTD., pp. 116-178 (1991).

Co-pending U.S. Appl. No. 11/223,961, filed Sep. 13, 2005.

Co-pending U.S. Appl. No. 11/223,149, filed Sep. 12, 2005.

French Search Report for French Appln. No. 04/09695, related to co-pending U.S. Appl. No. 11/223,961 (2005).

French Search Report for French Appln. No. 04/09693, related to co-pending U.S. Appl. No. 11/223,962 (2005).

French Search Report for French Appln. No. 04/09694, related to present U.S. Appl. No. 11/223,962 (2005).

Babichev, F.S. et al., "Cyanine Dyes from DiHydrooxazino- and Dihydrothiazino- Bennzthiazolium Salts," translated from *Zhurnal Organicheskoi Khimii*, vol. 1, No. 3, pp. 562-570, Mar. 1965.

Babichev, F.S. et al., "Styryl Dyes, Mero- and Rhodacyanine from 2,3- Polymethylenebenzothiazolium Salts," translated from *Zhurnal Obshehei Khimii*, vol. 34, No. 7, pp. 2433-2440, Jul. 1964.

STIC Search report dated Jun. 5, 2007, cited in copending U.S. Appl. No. 11/223,149.

Office Action dated Oct. 10, 2007, in copending U.S. Appl. No. 11/223,149.

Notice of Allowance and Fee Due dated Jan. 9, 2008, in copending U.S. Appl. No. 11/223,149, Examiner E. Elhilo.

English Abstract of JP Publication No. 80012407. (1980).

STIC search report dated Jun. 6, 2007, cited in copending U.S. Appl. No. 11/223,961.

Non-Final Rejection dated Oct. 23, 2007, copending U.S. Appl. No. 11/223,961, Examiner E. Elhilo.

Daltrozzo E. et al., "Tautomerism od Quinoline Red dyes," STN Database accession No. 1966:104990.

Notice of Allowance and Fee Due dated Apr. 17, 2008, co-pending U.S. Appl. No. 11/223,149.

* cited by examiner

COMPOSITION COMPRISING AT LEAST ONE SUBSTITUTED CARBOCYANIN DERIVATIVE, PROCESS FOR TREATING KERATIN FIBERS USING IT, DEVICE THEREFOR AND USE THEREOF

CROSS-REFERENCE TO RELATED APPLICATIONS

This application claims benefit of U.S. Provisional Application No. 60/616,526, filed Oct. 7, 2004, the contents of which are incorporated herein by reference. This application also claims benefit of priority under 35 U.S.C. § 119 to French Patent Application No. 04 09064 filed Sep. 13, 2004, the contents of which are also incorporated by reference.

FIELD OF THE INVENTION

The present disclosure pertains to a composition comprising, in a cosmetically acceptable medium, at least one direct dye. The present disclosure also relates to a process for treating keratin fibers using this composition, and also to a device comprising it. Finally, the present disclosure relates to a process for applying the composition according to the disclosure as a coloring agent for the said fibers.

The present disclosure relates to the field of dyeing keratin fibers, for example, dyeing the hair.

BACKGROUND OF THE INVENTION

There are essentially two types of dyeing.

The first is semi-permanent dyeing or direct dyeing, which involves dyes capable of giving the hair's natural color a more or less pronounced change.

The dyes used are colored and coloring substances that have a certain affinity for keratin fibers.

It should be noted that this type of dyeing fades out after several washes, which may be an inconvenience.

When it is desired to obtain a coloration that is lighter than the original color of the fibers, it is necessary to use, with the direct dyes, at least one oxidizing agent, under alkaline pH conditions.

However, these conditions of use are not free of consequences on the properties of the treated fibers. Specifically, in the long run, the fibers are more or less degraded and have a tendency to become coarse, dull, brittle and difficult to style.

The second is permanent dyeing or oxidation dyeing. This is performed with oxidation dye precursors, which are colorless or weakly colored compounds, comprising at least one oxidation base optionally combined with at least one coupler. Once mixed with oxidizing products, at the time of use, the precursors give rise to colored compounds and dyes via a process of oxidative condensation.

Given the necessary presence of an oxidizing agent in this type of dyeing, the drawbacks mentioned above also occur in this case.

Moreover, it has been shown that fluorescent dyes may be advantageous in hair dyeing. However, the stability on storage of compositions containing standard fluorescent dyes can be improved.

Moreover, it would also be advantageous to further enhance the wash-fastness and shampoo-fastness of the colorations obtained using these compositions.

DETAILED DESCRIPTION OF THE INVENTION

It has been found, entirely unexpectedly, that compositions comprising at least one direct compound corresponding to a particular substituted carbocyanin derivative may allow satisfactory dyeing results to be obtained, with good stability of the compositions. Moreover, most of the compounds used in the context of the present disclosure have the advantage of being fluorescent, and their use may allow the problem mentioned above to be solved.

Disclosed herein is a composition for dyeing keratin fibers, for example, human keratin fibers, comprising, in a cosmetically acceptable medium comprising water or a mixture of water and at least one organic solvent, at least one direct dye that is soluble in the medium, of formula (I) or (I'):

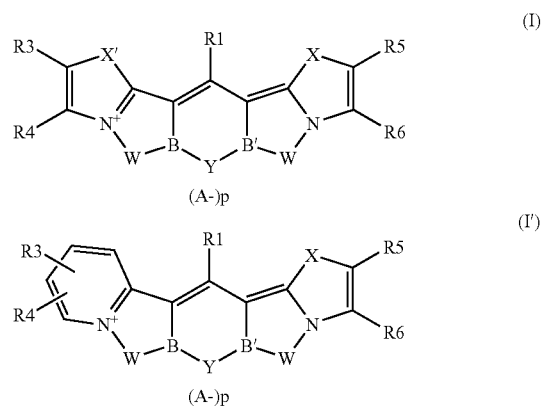

wherein:
R1 is chosen from:
  hydrogen atoms,
  linear, branched or cyclic alkyl radicals comprising from 1 to 22 carbon atoms, optionally substituted with at least one group chosen from
    hydroxyl,
    linear or branched $C_1$-$C_6$ alkoxy,
    $C_1$-$C_6$ cycloalkoxy, and
    phenyl, optionally substituted with at least one carboxyl group,
  $C_6$-$C_{30}$ aryl radicals, and
  amino radicals substituted with at least one radical chosen from linear or branched $C_1$-$C_6$ alkyls or hydroxyalkyls;
R3, R4, R5 and R6, which may be identical or different, are each chosen from:
  hydrogen atoms;
  linear or branched alkyl radicals comprising from 1 to 22 carbon atoms, optionally substituted with at least one hydroxyl radicals;
  halogen atoms,
  carboxyl radicals, and
  sulfo radicals;

or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle; wherein each aliphatic or aromatic ring or heterocycle are optionally substituted with at least one substituent chosen from:
  halogen atoms,
  $C_1$-$C_6$ alkoxy radicals, carboxyl radicals,
sulfo radicals and
$C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group, B and B', which may be identical or different, are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, ($C_6$-$C_{30}$)aryloxy($C_1$-$C_6$)alkyls or ($C_1$-$C_4$)alkyl($C_6$-$C_{30}$)-arylaminos;

X and X', which may be identical or different, are each chosen from O, S, N, NR'7, Se and CR'8R'9;

Y is chosen from O, S, N, Se, NR7, CO and CR8R9;

R8 and R9, which may be identical or different, are each chosen from
hydrogen atoms; and
linear or branched $C_1$-$C_{22}$ alkyl radicals optionally substituted with at least one group chosen from
hydroxyls,
$C_1$-$C_{10}$ mono- or dialkylaminos,
$C_1$-$C_{10}$ mono- or dihydroxyalkylaminos,
$C_{10}$-$C_{30}$ aryls,
$C_{10}$-$C_{30}$ aryloxys and
($C_2$-$C_{10}$)acylaminos;

R7 is chosen from
hydrogen atoms,
linear or branched $C_1$-$C_{10}$ alkyl radicals,
$C_6$-$C_{30}$ aryl radicals,
amino radicals bearing at least one $C_6$-$C_{30}$ aryl radical optionally substituted with at least one substituent chosen from
$C_1$-$C_6$ alkyl radicals
carboxyl radicals,
($C_1$-$C_4$)alkyl($C_6$-$C_{30}$)arylsulfonyl radicals,
$C_2$-$C_{10}$ acyl radicals,
tri($C_1$-$C_4$)alkylamino($C_1$-$C_4$)alkylcarbonyl radicals, and
aminothiocarbonyl groups;

Z and
N=Z,
wherein Z is chosen from an optionally fused 5- or 6-membered heterocycle comprsiing from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and ($C_1$-$C_4$) alkoxycarbonyl($C_1$-$C_6$)alkyl radicals;

p is an number ranging from 0 to 1; and $A^-$ is chosen from organic anions and mineral anions, or a mixture of anions.

An embodiment of the disclosure is process for treating keratin fibers, for example, human keratin fibers, wherein the composition as disclosed above is applied to said wet or dry fibers, for a time that is sufficient to develop the coloration, after which the fibers are rinsed, optionally washed with shampoo, rinsed again and dried, or the resulting fibers are left to dry.

In another embodiment, the composition according to the disclosure is applied to said wet or dry fibers, without final rinsing.

Another embodiment of the disclosure is a multi-compartment device, wherein at least one compartment comprises the composition as dislcosed above and at least one other compartment comprises an oxidizing agent.

Finally, the disclosure relates to a process for dyeing keratin materials, for example, human keratin fibers, comprising applying to said fibers at least one composition as dislcosed above.

However, other characteristics and advantages of the disclosure will emerge more clearly on reading the description and the examples that follow.

As used herein, the term "human keratin fibers" means the hair, the eyelashes and the eyebrows.

In one embodiment, the composition is suitable for treating keratin fibers, for example, human keratin fibers, irrespective of their coloration before treatment and whether or not this coloration is natural or artificially obtained.

According to one embodiment, the composition is intended to be applied to dark keratin fibers, for example, human keratin fibers. For example, the dark keratin fibers are pigmented or artificially dyed fibers, the tone height of which is less than or equal to 6, for example, less than or equal to 4.

In one embodiment, the mesomeric forms of the compounds of formula (I) or (I') also form part of the context of the present disclosure.

In another embodiment, the compounds of formula (I) or (I') are fluorescent dyes.

As used herein, "fluorescent dye" means a molecule that colors by itself, is soluble in the medium, and absorbs light of the visible spectrum and also possibly of the ultraviolet spectrum (wavelengths ranging from 360 to 760 nm), but which, unlike a standard dye, converts a portion of the absorbed energy into fluorescent light of longer wavelength than that of the absorbed light, emitted in the visible part of the spectrum.

According to another embodiment, the radical R1 is chosen from hydrogen atoms and unsubstituted linear or branched $C_1$-$C_{16}$ alkyl radicals.

According to another embodiment, Y is chosen from O, N, NR7 and CO.

According to another embodiment, X and X', which may be the same or different, are each chosen from a sulfur atom, an oxygen atom or a group NR'7 wherein R'7 is chosen from $C_1$-$C_4$ alkyl radicals.

According to another embodiment, X and X' are identical.

According to another embodiment, W is an ethylene radical.

According to another embodiment, B and B', which may the the same or different, are each chosen from carbon atoms or CH groups.

According to another embodiment, R3 and R4 and/or R5 and R6 together with the carbon atoms to which each is attached, form 6- to 30-membered aliphatic or aromatic rings or heterocycles, fused to an identical or different 6- to 30-membered aromatic ring or heterocycle; wherein each aliphatic or aromatic ring or heterocycle is optionally substituted with at least one substituent chosen from
halogen atoms,
$C_1$-$C_6$ alkoxy radicals,
carboxyl radicals,
sulfo radical and
$C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group.

According to another embodiment, A⁻ may be a mineral anion chosen from, for example, halides, sulfates, bisulfates, nitrates, phosphates, hydrogen phosphates, dihydrogen phosphates, carbonates and bicarbonates.

According to another embodiment, A may be an organic anion chosen from, for exmaple, anions originating from salts of saturated or unsaturated, aromatic or non-aromatic sulfuric, sulfonic, mono- or polycarboxylic acids, optionally substituted with at least one hydroxyl or amino radical and halogen atoms.

For example, A⁻ may be chosen from chloride, iodide, sulfate, methosulfate and ethosulfate.

According to another embodiment, the at least one direct dye of formula (I) or (I') is soluble in the cosmetically acceptable medium.

According to another embodiment, the at least one direct dye may be soluble in the medium of the composition to at least 1 gram per liter, for example, to at least 5 grams per liter at a temperature of 25° C.

According to another embodiment, the at least one direct dye is chosen from:

Benzimidazo[2,1-f]benzimidazo[1',2':1,2[pyrido[4,3-b][1,6]naphthyridinium, 2,3, 13, 14-tetrachloro-16, 18-diethyl-6,7,7a,8,8a,9,10,16-octahydro-8-[(4-methylphenyl)amino], iodide

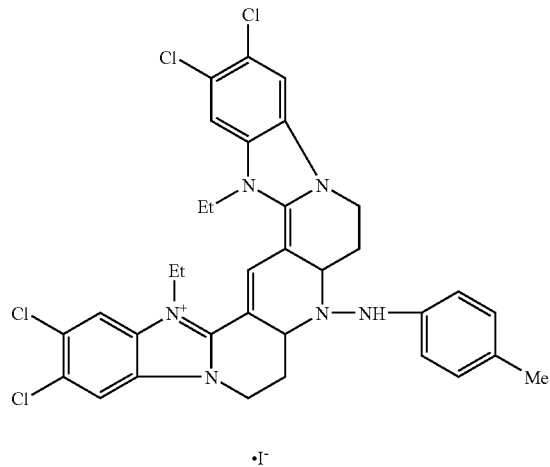

6H-Benzothiazolo[2,3-f]benzothiazolo[3',2':1,2[pyrido[4,3-b][1,6]naphthyridin-5-ium, 8-(2-benzothiazolylamino)-7,7a,8,8a,9,10-hexahydro, iodide

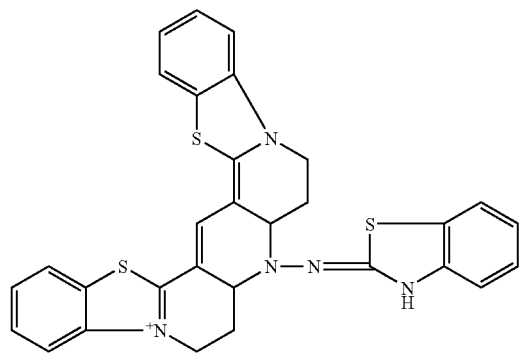

6H-Benzothiazolo[2,3-f]benzothiazolo[3',2':1,2[pyrido
[4,3-b][1,6]naphthyridin-5-ium,
7,7a,8,8a,9,10-hexahydro-8-[[trimethylammonio)acetyl]-
amino]-, chloride iodide
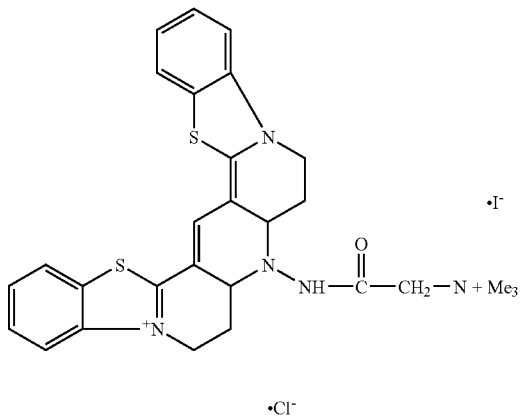
6H-Benzothiazolo[2,3-f]benzothiazolo[3',2':1,2[pyrido
[4,3-b][1,6]naphthyridin-5-ium,
7,7a,8,8a,9,10-hexahydro-8-(4-oxo-2-thioxo-3-thiazolidinyl),
iodide
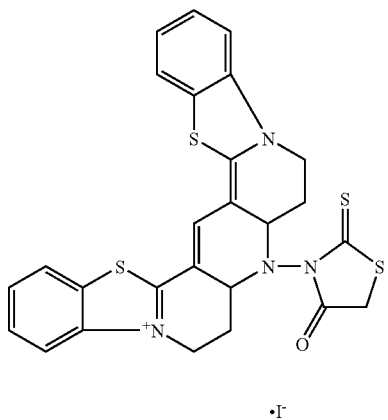
6H-Benzothiazolo[2,3-f]benzothiazolo[3',2':1,2[pyrido
[4,3-b][1,6]naphthyridin-5-ium,
7,7a,8,8a,9,10-hexahydro-8-[[(4-methylphenyl)sulfonyl],
amino], iodide
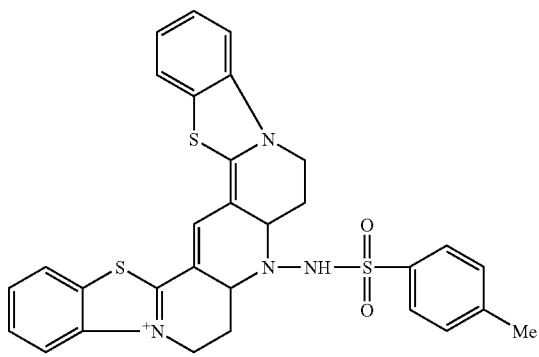

-continued
6H-Benzothiazolo[2,3-f]benzothiazolo[3',2':1,2[pyrido[4,3-b][1,6]naphthyridin-5-ium, 8-[(1,1-dioxido-1,2-benzisothiazol-3-yl)amino] 7,7a,8,8a,9,10-hexahydro, iodide
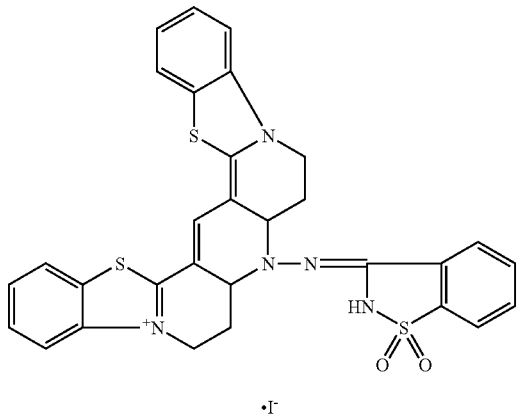
6H-Pyrano[3'',2'':3,4;-5'',6'':3',4'] dipyrido[1,2-a:1',2'-a'] bisbenzimidazolium, 2,3,13,14-tetrachloro-16,18-diethyl-7,7a,8a,9,10,16-hexahydro, trifluoroacetate
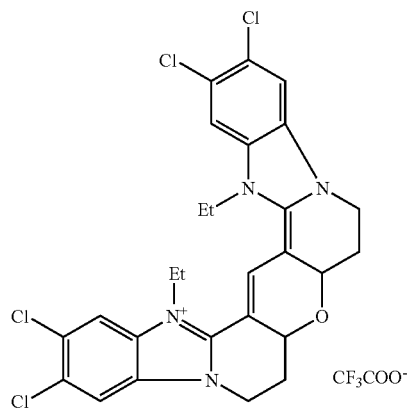
6H,10H-Pyrano[3'',2'':3,4;-5'',6'':3',4'] dipyrido[2,1-b:2',1'-b'] bisbenzoxazol-5-ium, 17-ethyl-7,7a,8a,9-tetrahydro-3,13-diphenyl, bromide
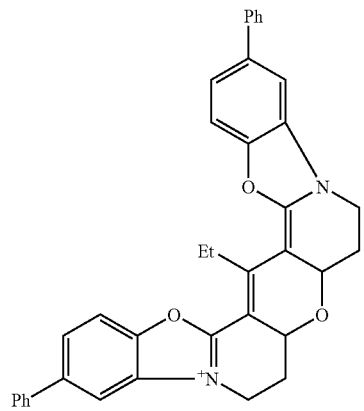

6H,10H-Pyrano[3",2":3,4;-5",6":3',4']
dipyrido[2,1-b:2',1'-b']
bisbenzothiazol-5-ium, 7,7a,8a,9-tetrahydro-3,13-
dimethoxy, iodide
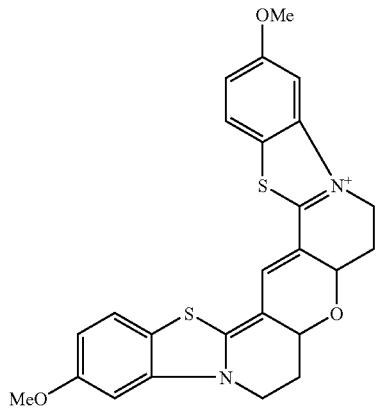
6H,10H-Pyrano[3",2":3,4;-5",6":3',4']
dipyrido[2,1-b:2',1'-b']
bisbenzthiazol-5-ium, 17-ethyl-7,7a,8a,9-
tetrahydro, bromide
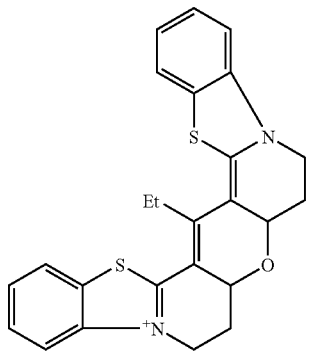
6H,10H-Pyrano[3",2":3,4;-5",6":3',4']
dipyrido[2,1-b:2',1'-b']
bisbenzthiazol-5-ium, 7,7a,8a,9-
tetrahydro, iodide
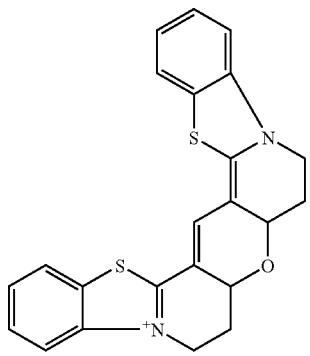

-continued
6H-Benzoxazolo[2,3-f]benzoxazolo[3',2':1,2]pyrido[4,3-b]
[1,6]naphthyridin-5-ium, 8-(2-benzothiazolylamino)-
7,7a,8,8a,9,10-hexahydro-3,13-diphenyl, bromide
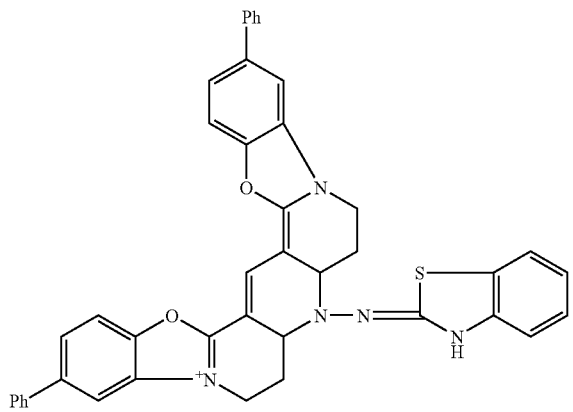
6H-Benzothiazolo[2,3-f]benzothiazolo[3',2':1,2]pyrido[4,3-b]
[1,6]naphthyridin-5-ium, 8-(2-benzothiazolylamino)-
7,7a,8,8a,9,10-hexahydro, bromide
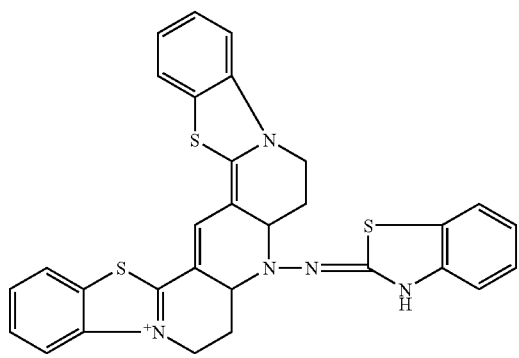
6H-Benzothiazolo[2,3-f]benzothiazolo[3',2':1,2]pyrido[4,3-b]
[1,6]naphthyridin-5-ium, 8-[(aminothioxomethyl)
amino]7,7a,8,8a,9,10-hexahydro, iodide
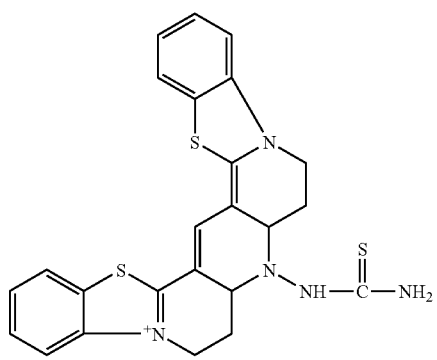

-continued

6H-Benzimidazo[2,1-f]benzimidazo[1',2':1,2]pyrido[4,3-b][1,6]naphthyridin-5-ium, 2,3,13,14-tetrachloro-16,18-diethyl-7,7a,8,8a,9,10,16,18-octahydro-9-[(4-methylphenyl)amino]iodide

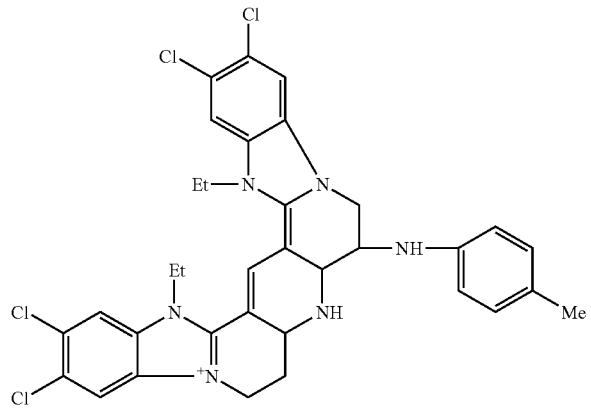

9H-Bisbenzimidazo[2',1':3,4]-pyrazino[1,2-c2',1'-f]pyrimidin-5-ium,6,7,11,12,18,20-hexahydro-9-oxo-,chloride

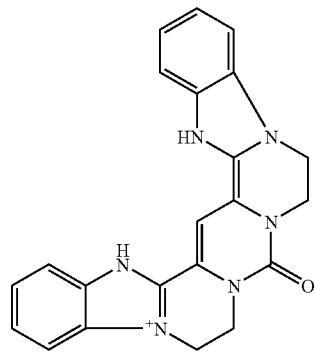

Internal salt of pyrano-[3'',2'':3,4;5'',6'':3',4']dipyrido[1,2-a:1',2'-a']diindol-5-ium, 2-(aminomethyl)-6,7,9,10,16,18-hexahydro-16,16,18,18-tetramethyl-14-sulfo-

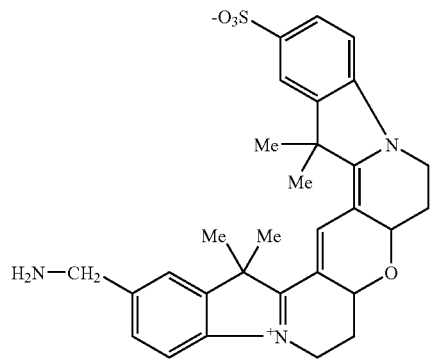

Internal salt of pyrano-[3'',2'':3,4;5'',6'':3',4']dipyrido[1,2-a:1',2'-a']diindol-5-ium, 2-(carboxymethyl)-6,7,9,10,16,18-hexahydro-16,16,18,18-tetramethyl-14-sulfo

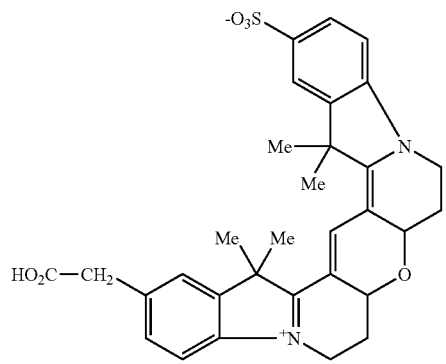

-continued

Internal salt of pyrano-[3'',2'':3,4;5'',6'':3',4']dipyrido[1,2-a:1',2'-a']diindol-5-ium, 2,14-bis(carboxymethyl)-6,7,9,10,16,18-hexahydro-16,16,18,18-tetramethyl

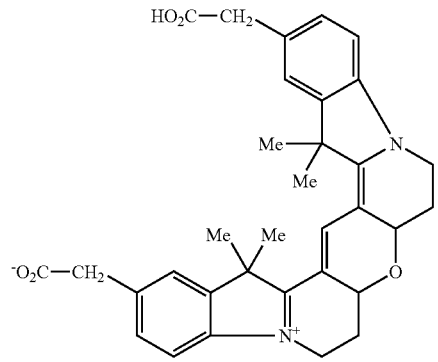

Internal salt of 6H-benz[2'',3'']indolizino-[8',7':5,6]pyrano[3,2-a]benzo[f]quinolizin-5-ium, 14-(carboxymethyl)-7,7a,8a,9,10,16-hexahydro-16,16-dimethyl

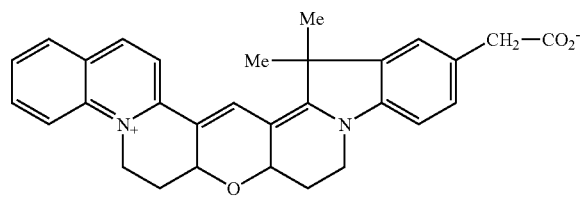

Internal salt of 6H-benz-[2,3]indolizino[7,8-b]indolo[2,1-f][1,6]naphthyridin-5-ium, 8-[(4-carboxyphenyl)amino]-7,7a,8,8a,9,10,16,18-octahydro-16,16,18,18-tetramethyl

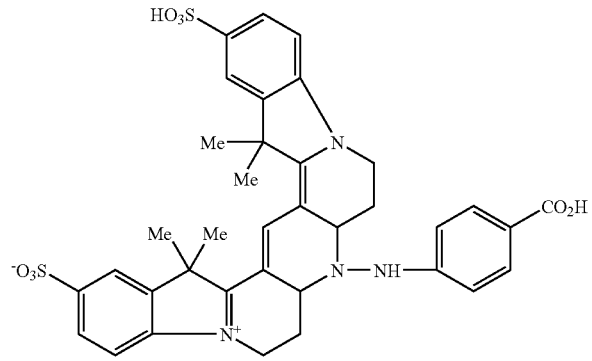

Internal salt of 10H-benz[2'',3'']indolizino-[8'',7'':5',6']pyrano[3',2':3,4]pyrido[2,1-b]benzothiazol-5-ium, 2-(carboxymethyl)-6,7,7a,8a,9,18-hexahydro-18,18-dimethyl

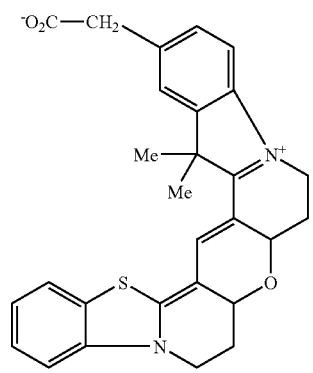

Internal salt of pyrano-[3'',2'':3,4;5'',6'':3',4']dipyrido[1,2-a:1',2'-a']diindol-5-ium, 6,7,9,10,16,18-hexahydro-2-(2-hydroxyethyl)-16,16,18,18-tetramethyl-14-sulfo

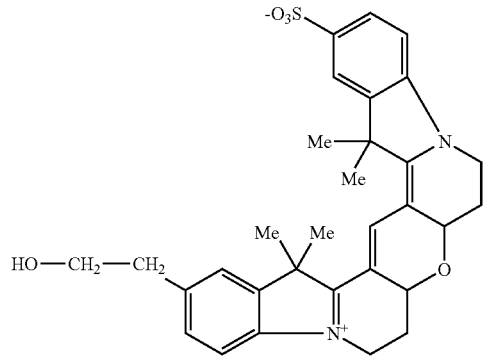

Internal salt of pyrano-[3'',2'':3,4;5'',6'':3',4']dipyrido[1,2-a:1',2'-a']diindol-5-ium, 2-[(formylamino)methyl]-6,7,9,10,16,18-hexahydro-16,16,18,18-tetramethyl-14-sulfo

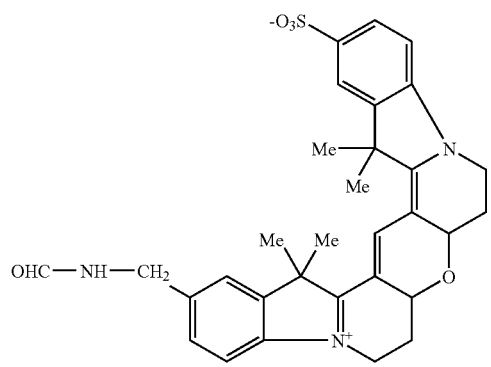

Internal salt of pyrano-[3'',2'':3,4;5'',6'':3',4']dipyrido[1,2-a:1',2'-a']diindol-5-ium, 2-[2-[(2-aminoethyl)amino]2-oxoethyl]-6,7,9,10,16,18-hexahydro-16,16,18,18-tetramethyl-14-sulfo

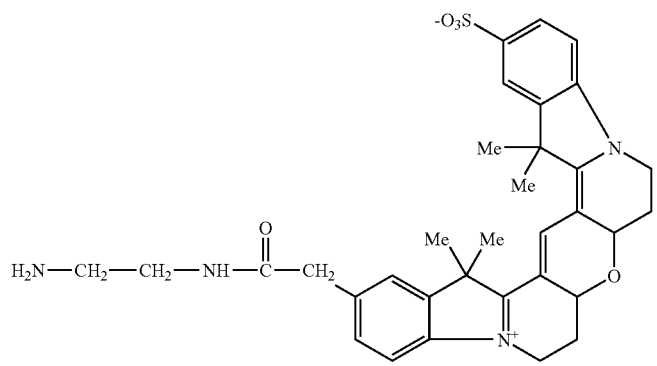

Internal salt of pyrano-[3'',2'':3,4;5'',6'':3',4']dipyrido[1,2-a:1',2'-a']diindol-5-ium, 2-[2-[(2-carboxymethyl)amino]-2-oxoethyl]-6,7,9,10,16,18-hexahydro-,16,16,18,18-tetramethyl-14-sulfo

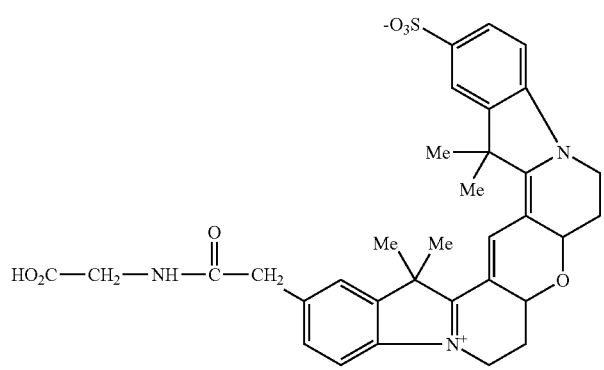

-continued

Internal salt of dibenzo[e,e]'pyrano-[3'',2'':3,4;5'',3':4']dipyrido[1,2-a:1',2'-a']diindol-7-ium, 8,9,11,12,20,22-hexahydro-20,20,22,22-tetramethyl-3,17-disulfo

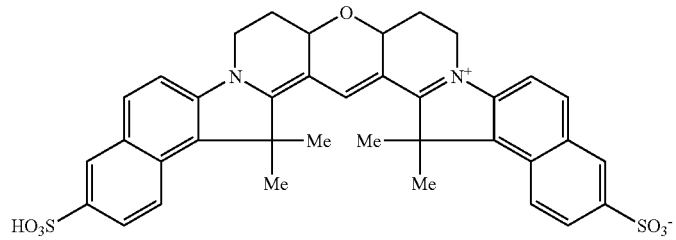

Salt (for example, chloride) of 7H,11H-Bisnaphth[2',3':4,5]oxazolo[3,2-a:3',2'-a']pyrano[3,2-c:5,6-c']dipyridin-6-ium

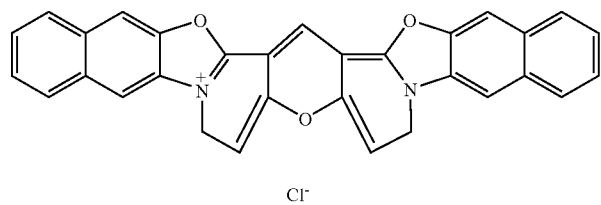

Salt (for example, chloride) of 7H,11H-bisnaphth[2',3':4,5]oxazolo[3,2-a:3',2'-a']pyrano[3,2-c:5,6-c']dipyridin-6-ium, 20-ethyl-8,8a,9a,10-tetrahydro-8,10-bis(3-phenoxypropyl)-, 4-methylbenzenesulfonate

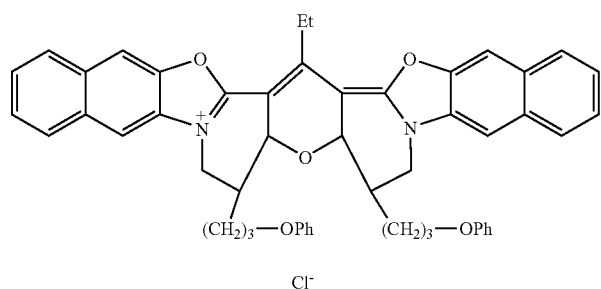

Salt (for example, chloride) of 7H,11H-bisnaphth[2',3':4,5]oxazolo[3,2-a:3',2'-a']pyrano[3,2-c:5,6-c']dipyridin-6-ium, 8,8a,9a,10-tetrahydro-8,10-bis(3-phenoxypropyl)-

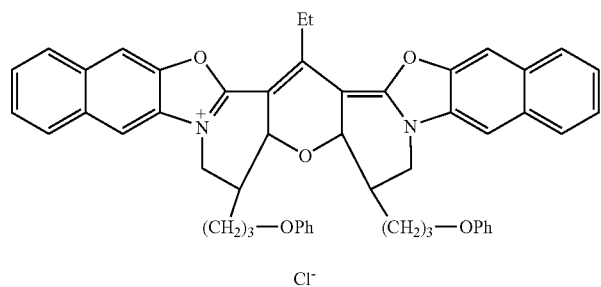

Salt (for example, chloride) of 6H,10H-naphtho[1'''',2'''':-4''',5''']thiazolo[3''',2'':1'',2'']pyrido[3'',4'':5',6']pyrano[3',2':3,4]pyrido[2,1-b]benzoxazol

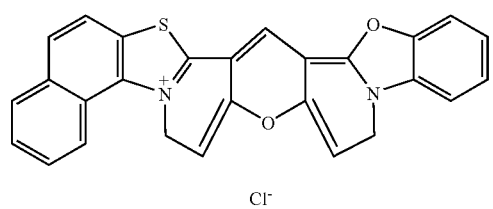

-continued
6H,10H-Pyrano[3",2":3,4;-5",6":3',4']dipyrido[2,1-b:2',1'-b']bisbenzothiazol-5-ium, 7,7a,8a,9-tetrahydro, bromide
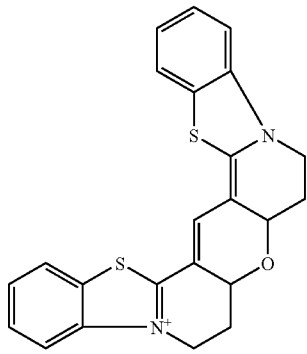
Salt (for example, chloride) of 10H-benz[2",3"]indolizino[8",7":5',6']pyrano[3',2':3,4]pyrido[2,1-b]benzothiazol-5-ium
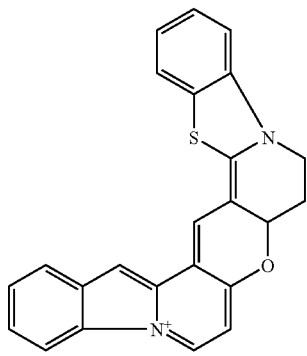
Salt (for example, chloride) of dibenzo[e,e']pyrano[3",2":-3,4;5",6":3',4']dipyrido[1,2-a:1',2'-a']diindol-7-
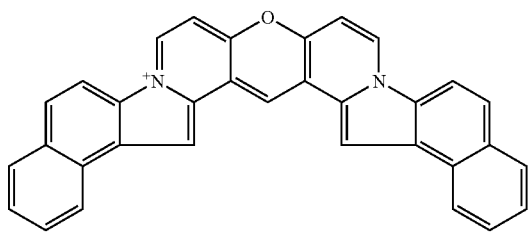
Salt (for example, chloride) of pyrano[3",2":3,4;5",6":3',4']dipyrido[1,2-a:1',2'-a']diindol-5-ium
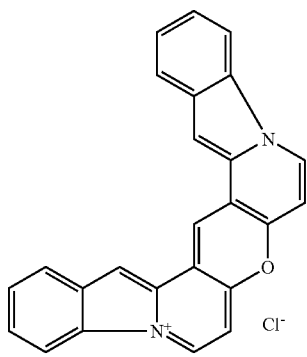

| | |
|---|---|
| Salt (for example, chloride) of 1H-benz[2,3]indolizino[7,8-b]indolo[2,1-f][1,6]naphthyridin-5-ium | 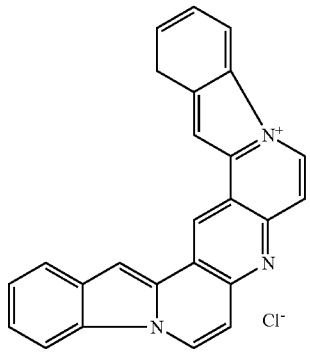 |
| 6H,10H-Pyrano[3",2":3,4;-5",6":3',4']dipyrido[2,1-b:2',1'-b']bisbenzothiazol-5-ium, 7,7a,8a,9-tetrahydro-, heptafluorobutanoate | 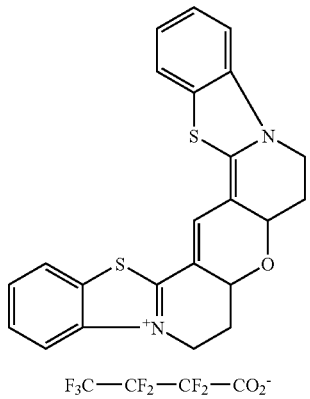 |
| 6H-Pyrano[3",2":3,4;-5",6":3',4']dipyrido[1,2-a:1',2'-a']bisbenzimidazolium, 2,3,13,14-tetrachloro-16,18-diethyl-7,7a,8a,9,10,16-hexahydro sulfate | 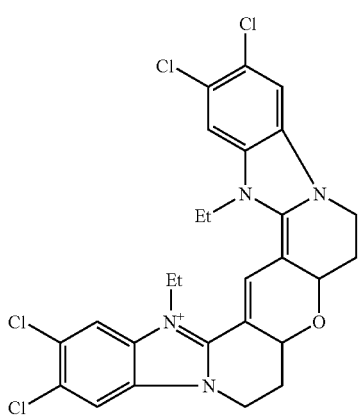 |
| Salt (for example, chloride) of 6H-benzothiazolo[2,3-f]benzothiazolo[3',2':1,2]pyrano[4,3-b][1,6]naphthyridin-5-ium, 8-(acetylamino)-7,7a,8,8a,9,10-hexahydro | 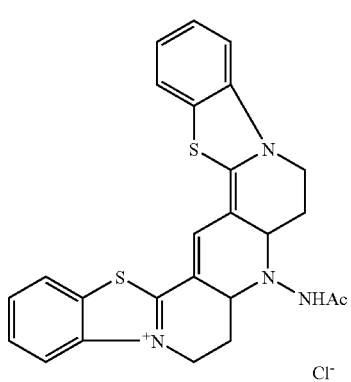 |

-continued

Salt (for example, chloride) of 1H-benzimidazo[2,1-f]benzimidazo[1',2':1,2]pyrido[4,3-b][1,6]naphthyridin-5-ium

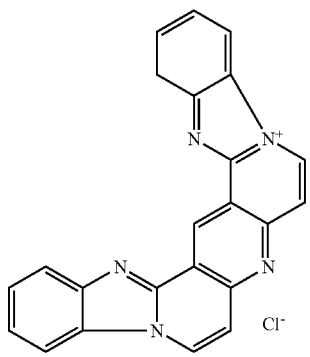

Benzimidazo[2,1-f]benzimidazo[1',2':1,2]pyrido[4,3-b][1,6]naphthyridinium, 2,3,13,14-tetrachloro-16,18-diethyl-6,7,7a,8,8a,9,10,16-octohydro-8-[(4-methylphenyl)amino]-, iodide

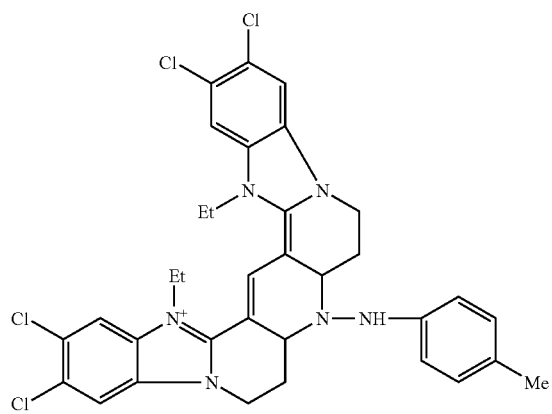

Salt (for example, chloride) of pyrano[3",2":3,4;5",6": 3',4']dipyrido[1,2-a:1',2'-a']bisbenzimidazol-5-

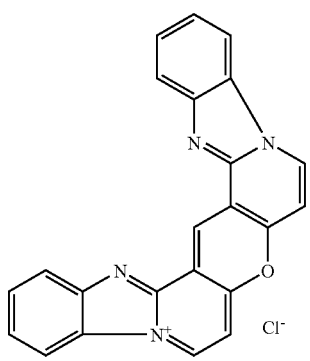

Salt (for example, chloride) of 6H,10H-pyrano[3",2":3,4;-5",6":3',4']dipyrido[2,1-b:2',1'-b']bisbenzothiazol-5-ium

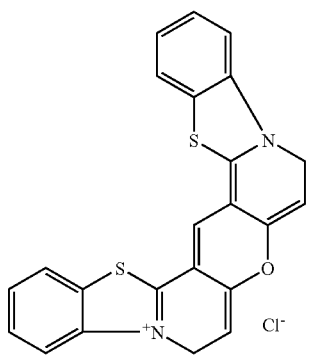

-continued
Salt (for example, chloride) of 6H-benzothiazolo[2,3-f]benzothiazolo[3',2':1,2]pyrido[4,3-b]naphthyridin-5-ium
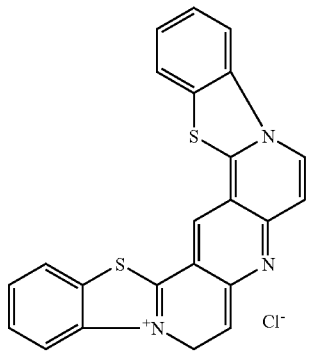
Salt (for example, chloride) of 6H,10H-pyrano[3'',2'':3,4;5'',6'':3',4']dipyrido[2,1-b:2',1'-b']bisbenzoxazol-5-
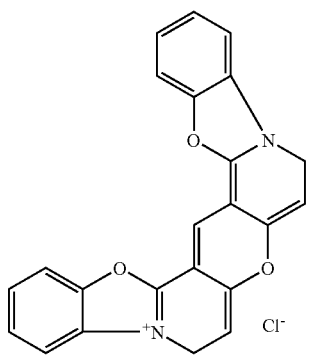
Salt (for example, chloride) of 6H-benzoxazolo[2,3-f]benzoxazolo[3',2':1,2]pyrido[4,3-b][1,6]naphthyridin-5-ium
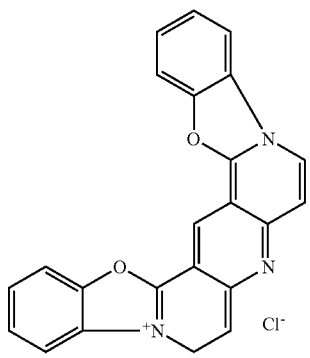
Salt (for example, chloride) of 6H-benzimidazo[2,3-f]benzimidazo[1',2':1,2]pyrido[4,3-b][1,6]naphthyridin-5-ium
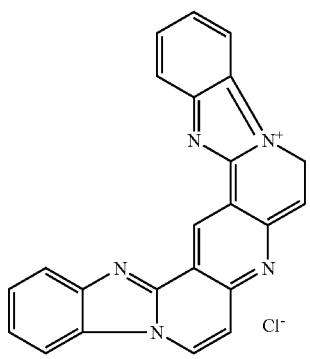

-continued

| | |
|---|---|
| 6H-Benzothiazolo[2,3-f]benzothiazolo[3',2':1,2]pyrido[4,3-b][1,6]naphthyridin-5-ium, 8-(acetylamino)-7,7a,8,8a,9,10-hexahydro-, dichloroiodate | 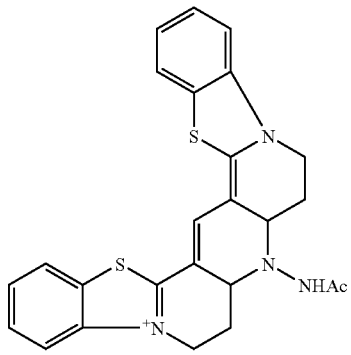 |
| 6,7,11,12-Tetrahydro-9-oxo-9H-bisthiazolo[3,2-a:3',2'-a']pyrimido[6,1-c:4,3-c']dipyrazin-5-ium chloride | 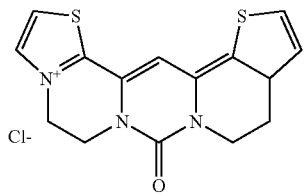 |
| 6,7,11,12-Tetrahydro-9-oxo-9H-bisoxazolo[3,2-a:3',2'-a']pyrimido[6,1-c:4,3-c']dipyrazin-5-ium bromide | 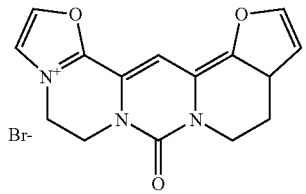 |
| 6,7,11,12-Tetrahydro-9-oxo-9H-bisselenazolo[3,2-a:3',2'-a']pyrimido[6,1-c:4,3-c']dipyrazin-5-ium bromide | 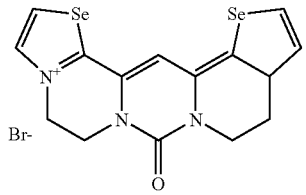 |

The selection of the counterion is not critical. Thus, the anions mentioned in the above table are given merely as examples.

The at least one direct dye of formula (I) or (I') may be present in an amount ranging from 0.01% to 20%, for example, from 0.1% to 5% by weight, relative to the total weight of the composition.

The cosmetically acceptable medium generally consists of water or of a mixture of water and of at least one organic solvent.

The at least one organic solvent may be chosen from $C_1$-$C_4$ linear or branched alkanols, for exmaple, ethanol and isopropanol; glycerol; glycols and glycol ethers, for example, 2-butoxyethanol, propylene glycol, dipropylene glycol, propylene glycol monomethyl ether, diethylene glycol monomethyl ether and monoethyl ether, and also aromatic alcohols, for example, benzyl alcohol or phenoxyethanol, similar products and mixtures thereof.

The at least one organic solvent may be present in an amount ranging from 1% to 40% by weight, for example, from 5% to 30% by weight, relative to the total weight of the dye composition.

According to one embodiment, the pH of the composition disclosed herein may range from 3 to 12, for example, from 5 to 11. It may be adjusted to the desired value by means of acidifying or basifying agents usually used in the dyeing of human keratin fibers.

Non-limiting examples of acidifying agents that may be mentioned include mineral or organic acids, for example, hydrochloric acid, orthophosphoric acid, sulfuric acid, carboxylic acids, for instance acetic acid, tartaric acid, citric acid and lactic acid, and sulfonic acids.

Non-limiting examples of basifying agents that may be mentioned include aqueous ammonia, alkaline carbonates, alkanolamines, for example, monoethanolamine, diethanolamine and triethanolamine and derivatives thereof, sodium hydroxide, potassium hydroxide and the compounds of formula (II) below:

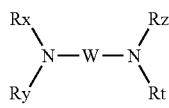

wherein
W is a propylene residue optionally substituted with a hydroxyl group or a $C_1$-$C_6$ alkyl radical;

$R_x$, $R_y$, $R_z$ and $R_t$, which may be identical or different, are each chosen from hydrogen atoms, $C_1$-$C_6$ alkyls and $C_1$-$C_6$ hydroxyalkyls.

According to another embodiment, the composition disclosed herein may also comprise at least one additional direct dyes of nonionic, cationic or anionic nature, and for example, cationic or nonionic, or combinations thereof.

For example, the at least one additional direct dye may be chosen from nitrobenzene dyes, azo, azomethine, methine, anthraquinone, naphthoquinone, benzoquinone, phenothiazine, indigoid, xanthene, phenanthridine, phthalocyanin, triarylmethane-based dyes and natural dyes, or mixtures thereof.

In one embodiment, the at least one additional direct dye may be chosen, for example, from the following red or orange nitrobenzene dyes:
 1-hydroxy-3-nitro-4-N-(γ-hydroxypropyl)aminobenzene,
 N-(β-hydroxyethyl)amino-3-nitro-4-aminobenzene,
 1-amino-3-methyl-4-N-(β-hydroxyethyl)amino-6-nitrobenzene,
 1-hydroxy-3-nitro-4-N-(β-hydroxyethyl)aminobenzene,
 1,4-diamino-2-nitrobenzene,
 1-amino-2-nitro-4-methylaminobenzene,
 N-(β-hydroxyethyl)-2-nitro-para-phenylenediamine,
 1-amino-2-nitro-4-(β-hydroxyethyl)amino-5-chlorobenzene,
 2-nitro-4-aminodiphenylamine,
 1-amino-3-nitro-6-hydroxybenzene,
 1-(β-aminoethyl)amino-2-nitro-4-(β-hydroxyethyloxy)benzene,
 1-(β,γ-dihydroxypropyl)oxy-3-nitro-4-(β-hydroxyethyl)aminobenzene,
 1-hydroxy-3-nitro-4-aminobenzene,
 1-hydroxy-2-amino-4,6-dinitrobenzene,
 1-methoxy-3-nitro-4-(β-hydroxyethyl)aminobenzene,
 2-nitro-4'-hydroxydiphenylamine, and
 1-amino-2-nitro-4-hydroxy-5-methylbenzene.

In another embodiment, the composition may also comprise, in addition to or instead of these nitrobenzene dyes, at least one additional direct dye chosen from yellow, green-yellow, blue or violet nitrobenzene dyes, azo dyes, anthraquinone dyes, naphthoquinone dyes, benzoquinone dyes, indigoid dyes, and triarylmethane-based dyes.

The at least one additional direct dye may, for example, be basic dyes, among which non-limiting mention may be made of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99", or acidic direct dyes, among which non-limiting mention may be made of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43" and "Acid Blue 62", or alternatively cationic direct dyes such as those described in PCT Patent Publication Nos. WO 95/01772, and WO 95/15144 and European Patent No. EP 714 954, the content of which forms an integral part of the present disclosure.

Among the additional yellow and green-yellow nitrobenzene direct dyes that may be mentioned, for example, are the compounds chosen from:
 1-β-hydroxyethyloxy-3-methylamino-4-nitrobenzene,
 1-methylamino-2-nitro-5-(β,γ-dihydroxypropyl)oxybenzene,
 1-(β-hydroxyethyl)amino-2-methoxy-4-nitrobenzene,
 1-(β-aminoethyl)amino-2-nitro-5-methoxybenzene,
 1,3-di(β-hydroxyethyl)amino-4-nitro-6-chlorobenzene,
 1-amino-2-nitro-6-methylbenzene,
 1-(β-hydroxyethyl)amino-2-hydroxy-4-nitrobenzene,
 N-(β-hydroxyethyl)-2-nitro-4-trifluoromethylaniline,
 4-(β-hydroxyethyl)amino-3-nitrobenzenesulfonic acid,
 4-ethylamino-3-nitrobenzoic acid,
 4-(β-hydroxyethyl)amino-3-nitrochlorobenzene,
 4-(β-hydroxyethyl)amino-3-nitromethylbenzene,
 4-(β,γ-dihydroxypropyl)amino-3-nitrotrifluoromethylbenzene,
 1-(β-ureidoethyl)amino-4-nitrobenzene,
 1,3-diamino-4-nitrobenzene,
 1-hydroxy-2-amino-5-nitrobenzene,
 1-amino-2-[tris(hydroxymethyl)methyl]amino-5-nitrobenzene,
 1-(β-hydroxyethyl)amino-2-nitrobenzene, and
 4-(β-hydroxyethyl)amino-3-nitrobenzamide.

Among the additional blue or violet nitrobenzene direct dyes that may be mentioned, for example, are the compounds chosen from:
 1-(β-hydroxyethyl)amino-4-N,N-bis(β-hydroxyethyl)amino-2-nitrobenzene,
 1-(γ-hydroxypropyl)amino-4, N,N-bis(β-hydroxyethyl)amino-2-nitrobenzene,
 1-(β-hydroxyethyl)amino-4-(N-methyl-N-β-hydroxyethyl)amino-2-nitrobenzene,
 1-(β-hydroxyethyl)amino-4-(N-ethyl-N-β-hydroxyethyl)amino-2-nitrobenzene,
 1-(β,γ-dihydroxypropyl)amino-4-(N-ethyl-N-β-hydroxyethyl)amino-2-nitrobenzene,
 2-nitro-para-phenylenediamines having the following formula:

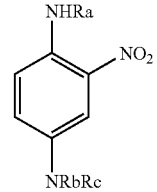

wherein:
 $R_b$ is chosen from $C_1$-$C_4$ alkyls, β-hydroxyethyls, β-hydroxypropyls and γ-hydroxypropyls;
 $R_a$ and $R_c$, which may be identical or different, are each chosen from β-hydroxyethyl, β-hydroxypropyl, γ-hydroxypropyl and β,γ-dihydroxypropyl radicals, wherein at least one of the radicals $R_b$, $R_c$ or $R_a$ is chosen from a γ-hydroxypropyl radical and $R_b$ and $R_c$ are not simultaneously a β-hydroxyethyl radical when $R_a$ is a γ-hydroxypropyl radical, such as those described in French Patent No. FR 2 692 572.

Natural direct dyes that non-limiting mention may be made inlcude henna, camomile and indigo.

In one embodiment, the at least one additional direct dye is present in an amount ranging from 0.0005% to 12% by weight, for example, from 0.005% to 6% by weight, relative to the total weight of the composition.

In one embodiment, the composition disclosed herein may be used for oxidation dyeing, wherein the cosmetic composition additionally comprises at least one oxidation base chosen from the oxidation bases conventionally used for oxidation dyeing and among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine and 4'-aminophenyl-1-(3-hydroxy)pyrrolidine, and the addition salts thereof with an acid or with an alkaline agent.

Among the para-phenylenediamines mentioned above, for example, are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid or with an alkaline agent.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid or with an alkaline agent.

Among the para-aminophenols that may be mentioned, further for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid or with an alkaline agent.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid or with an alkaline agent.

Among the heterocyclic bases that may be mentioned, for example, are pyridine derivatives, pyrimidine derivatives and pyrazole derivatives, and the addition salts thereof with an acid or with an alkaline agent.

In one embodiment, the at least one oxidation base may be present in an amount ranging from 0.0005% to 12% by weight, for example, from 0.005% to 6% by weight relative to the total weight of the composition.

When it is intended for oxidation dyeing, the composition disclosed herein may also comprise at least one coupler, for example, to modify or to enrich with glints the shades obtained using the at least one direct dyes and the at least one oxidation base(s).

The at least one coupler that may be used may be chosen from, for example, the couplers conventionally used in oxidation dyeing, and among which non-limiting mention may be made of meta-phenylenediamines, meta-aminophenols, meta-diphenols and heterocyclic couplers, and the addition salts thereof with an acid or with an alkaline agent.

For example, the at least one coupler may be chosen from chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, and the addition salts thereof with an acid or with an alkaline agent.

When they are present, the at least one coupler may be present in an amount ranging from 0.0001% to 10% by weight, for example, from 0.005% to 5% by weight, relative to the total weight of the composition.

In general, the addition salts with an acid that may be used in the context of the compositions of the disclosure (oxidation bases and couplers) are chosen from, for example, the hydrochlorides, hydrobromides, sulfates, citrates, succinates, tartrates, tosylates, benzenesulfonates, lactates and acetates.

The addition salts with an alkaline agent that may be used in the context of the compositions of the disclosure (oxidation bases and couplers) are chosen, for example, from the addition salts with alkali metals or alkaline-earth metals, with ammonia and with organic amines, including alkanolamines and the compounds of formula (II).

The composition in accordance with the disclosure may also comprise various adjuvants conventionally used in cosmetic compositions, for example, for dyeing human keratin fibers, such as anionic, cationic, nonionic, amphoteric or zwitterionic polymers or mixtures thereof, mineral thickeners, antioxidants, penetrating agents, sequestering agents, fragrances, buffers, dispersants, conditioners, for instance cations, cationic or amphoteric polymers, chitosans, volatile or non-volatile, modified or unmodified silicones, film-forming agents, ceramides, preserving agents, stabilizers and opacifiers.

According to one embodiment, the composition comprises at least one surfactant. The at least one surfactant may be chosen from, for example, anionic, amphoteric, nonionic, zwitterionic and cationic surfactants or mixtures thereof.

For example, the at least one surfactant that may be suitable for carrying out the present disclosure may be chosen from:

(i) Anionic Surfactant(s):

By way of example of anionic surfactants that can be used, alone or as mixtures, in the context of the present disclosure, non-limiting mention may be made of salts (for example, alkali metal salts, for example, sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$alkyl sulfosuccinates, $(C_6-C_{24})$alkyl ether sulfosuccinates, $(C_6-C_{24})$alkylamide sulfosuccinates; $(C_6-C_{24})$alkyl sulfoacetates; $(C_6-C_{24})$acyl sarcosinates; and $(C_6-C_{24})$acyl glutamates. It may also possible to use, for example, $(C_6-C_{24})$alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds, for example, comprising from 12 to 20 carbon atoms and the aryl radical, for example chosen from phenyl and benzyl groups. Among the anionic surfactants which can also be used, non-limiting mention may also be made of fatty acid salts such as oleic, ricinoleic, palmitic and stearic acid salts, coconut oil acid or hydrogenated coconut oil acid; acyl lactylates wherein the acyl radical may comprise from 8 to 20 carbon atoms. It is also possible to use alkyl D-galactoside uronic acids and their salts, polyoxyalkylenated $(C_6-C_{24})$alkyl ether carboxylic acids, polyoxyalkylenated $(C_6-C_{24})$alkylaryl ether carboxylic acids, polyoxyalkylenated $(C_6-C_{24})$alkylamido ether carboxylic acids and their salts, for example, those comprising from 2 to 50 alkylene oxide groups, for example, ethylene oxide groups, and mixtures thereof.

(ii) Nonionic Surfactant(s):

The nonionic surfactants are, themselves also, compounds that are well known (see, for example, "Handbook of Surfactants" by M. R. Porter, published by Blackie & Son (Glasgow and London), 1991, pp. 116-178) and their nature is not a critical factor in the context of the present disclosure. Thus, they may be chosen from, for example polyethoxylated or polypropoxylated, alkylphenols, alpha-diols or alcohols, having a fatty chain comprising, for example, 8 to 18 carbon atoms, wherein the number of ethylene oxide or propylene oxide groups may range from 2 to 50. Non-limiting mention may also be made of copolymers of ethylene oxide and of propylene oxide, condensates of ethylene oxide and of propylene oxide with fatty alcohols; polyethoxylated fatty amides, for example, ranging from 2 to 30 mol of ethylene oxide, polyglycerolated fatty amides comprising 1 to 5, for example, 1.5 to 4, glycerol groups; polyethoxylated fatty amines, for example, ranging from 2 to 30 mol of ethylene oxide; oxyethylenated fatty acid esters of sorbitan, for example, ranging from 2 to 30 mol of ethylene oxide; fatty acid esters of sucrose, fatty acid esters of polyethylene glycol, alkylpolyglycosides, N-alkylglucamine derivatives, and amine oxides such as $(C_{10}-C_{14})$alkylamine oxides or N-acylaminopropylmorpholine oxides.

(iii) Amphoteric or Zwitterionic Surfactant(s):

The amphoteric or zwitterionic surfactants may be chosen, for example, from aliphatic secondary or tertiary amine derivatives wherein the aliphatic radical is a linear or branched chain comprising 8 to 18 carbon atoms and comprising at least one water-solubilizing anionic group (for example carboxylate, sulfonate, sulfate, phosphate or phosphonate); non-limiting mention may also be made of $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines.

Among the amine derivatives, non-limiting mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

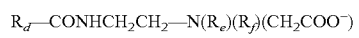

wherein:
$R_d$ is chosen from alkyl radicals of an acid $R_d$—COOH present in hydrolysed coconut oil, heptyl, nonyl or undecyl radicals,
$R_e$ is chosen from beta-hydroxyethyl groups and
$R_f$ is chosen from carboxymethyl groups; and

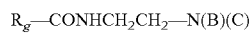

wherein:
B is chosen from —$CH_2CH_2OX$,
C is chosen from —$(CH_2)_z$—Y, wherein z is a number ranging from 1 or 2,
X is chosen from —$CH_2CH_2$—COOH groups and hydrogen atoms,
Y is chosen from —COOH and —$CH_2$—CHOH—$SO_3H$ radicals,
$R_g$ is chosen from alkyl radicals of an acid $R_g$—COOH present in coconut oil or in hydrolysed linseed oil, saturated radicals or radicals comprising at least one unsaturation, for example, $C_7$ to $C_{17}$, further, for example, $C_9$, $C_{11}$, $C_{13}$ or $C_{17}$ alkyl radicals or their iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, non-limiting mention may be made of the cocoamphodiacetate sold under the trade name Miranol® $C_2M$ concentrate by the company Rhodia Chimie.

(iv) Cationic Surfactants:

Among the cationic surfactants, non-limiting mention may be made of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium, or alkylpyridinium, chlorides or bromides; imidazoline derivatives; or amine oxides of cationic nature.

For example, the surfactants are nonionic, anionic or amphoteric, and further, for example, nonionic.

In one embodiment, the surfactants are present in an amount ranging from 0.01% to 50%, for example, from 0.1% to 25% by weight, relative to the total weight of the composition.

The composition may also comprise at least one thickening polymers. These polymers may be, for example, ionic or nonionic, and associative or non-associative.

As used herein, the term "non-associative thickening polymers" means thickening polymers not comprising a $C_{10}-C_{30}$ fatty chain.

Among the non-associative thickening polymers, non-limiting mention may be made of crosslinked acrylic acid homopolymers, crosslinked 2-acrylamido-2-methylpropanesulfonic acid homopolymers and the crosslinked acrylamide copolymers thereof, ammonium acrylate homopolymers or copolymers of ammonium acrylate and of acrylamide, nonionic guar gums, biopolysaccharide gums of microbial origin, gums originating from plant exudates, hydroxypropyl- or carboxymethyl celluloses; pectins and alginates, alone or as mixtures.

In one embodiment, the non-associative thickening polymers may be represented by crosslinked acrylic acid homopolymers.

For example, among the homopolymers of this type that may be mentioned are those crosslinked with an allylic ether of an alcohol of the sugar series, for instance the products sold under the names Carbopol 980, 981, 954, 2984 and 5984 by the company Noveon, or the products sold under the names Synthalen M and Synthalen K by the company 3 VSA.

The non-associative thickening polymers may also be chosen from, for example, crosslinked 2-acrylamido-2-methylpropanesulfonic acid homopolymers and the crosslinked acrylamide copolymers thereof.

The homopolymers and copolymers, which may be partially or totally neutralized, non-limiting mention may be made of polymers comprising from 90% to 99.9% by weight, relative to the total weight of polymer, of units of formula (j) below:

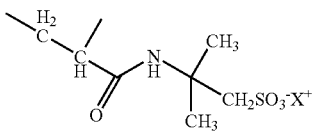

wherein $X^+$ is chosen from a cation, a mixture of cations, and a proton.

For example, the cations may be chosen from alkali metals (for instance sodium, or potassium), ammonium ions optionally substituted with 1 to 3 alkyl radicals, which may be identical or different, comprising from 1 to 6 carbon atoms, optionally bearing at least one hydroxyl radical, cations derived from N-methylglucamine or from basic amino acids, for instance arginine and lysine. For example, the cation is an ammonium, or sodium, ion.

For example, the polymer may comprise from 0.01% to 10% by weight, relative to the total weight of the polymer, of crosslinking units derived from at least one monomer comprising at least two ethylenic unsaturations (carbon-carbon double bond).

The crosslinking monomers comprising at least two ethylenic unsaturations may be chosen, for example, from diallyl ether, triallyl cyanurate, diallyl maleate, allyl(meth)acrylate, dipropylene glycol diallyl ether, polyglycol diallyl ethers, triethylene glycol divinyl ether, hydroquinone diallyl ether, tetraallyloxethanoyl, tetra- or diethylene glycol di(meth)acrylate, triallylamine, tetraallylethylenediamine, trimethylolpropanediallyl ether, trimethylolpropane triacrylate, methylenebis(meth)acrylamide or divinylbenzene, allylic ethers of alcohols of the sugar series, or other allylic or vinyl ethers of polyfunctional alcohols, and also allylic esters of phosphoric and vinylphosphonic acid derivatives, or mixtures of these compounds.

For further details regarding these polymers, reference may be made to European Patent No. EP 815 828.

Among the partially or totally neutralized crosslinked copolymers of 2-acrylamido-2-methylpropanesulfonic acid and of acrylamide, non-limiting mention may be made of the product described in Example 1 of European Patent No. EP 503 853, and reference may be made to the said document as regards these polymers.

The composition of the disclosure may also comprise, non-associative thickening polymers chosen from ammonium, acrylate homopolymers or copolymers of ammonium, acrylate and acrylamide.

For example, among the ammonium, acrylate homopolymers that may be mentioned is the product sold under the name Microsap PAS 5193 by the company Hoechst. For example, among the copolymers of ammonium, acrylate and of acrylamide that may be mentioned is the product sold under the name Bozepol C Nouveau or the product PAS 5193 sold by the company Hoechst. Reference may be made, for example, to documents French Patent No. FR 2 416 723, and U.S. Pat. Nos 2,798,053 and 2,923,692 as regards the description and preparation of such compounds.

The composition of the disclosure may also comprise dimethylaminoethyl methacrylate homopolymers quaternized with methyl chloride or dimethylaminoethyl methacrylate copolymers quaternized with methyl chloride and acrylamide.

Among the homopolymers of this type, non-limiting mention may be made of the products sold under the names Salcare 95 and Salcare 96 by the company Ciba-Allied Colloids. Among the copolymers of this family, non-limiting mention may be made of the product Salcare $SC_{92}$ sold by Ciba-Allied Colloids or the product PAS 5194 sold by Hoechst. These polymers may be described and prepared in European Patent No. EP 395 282, to which reference may be made.

The composition of the disclosure may also comprise nonionic guar gums, for instance the unmodified nonionic guar gums sold under the name Vidogum GH 175 by the company Unipectine and under the name Jaguar C by the company Meyhall.

For example, the nonionic guar gums that may be used according to the disclosure may be modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, for example, ranging from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall or under the name Galactasol 4H4FD2 by the company Aqualon.

As examples of suitable non-associative thickening polymers, non-limiting mention may also be made of biopolysaccharide gums of microbial origin, such as scleroglucan gum or xanthan gum.

For example, gums derived from plant exudates, such as gum arabic, ghatti gum, karaya gum and gum tragacanth; hydroxypropyl- or carboxymethyl celluloses; pectins and alginates, may also be suitable.

These polymers are well known to those skilled in the art and are described in Robert L. Davidson's book entitled "Handbook of Water soluble gums and resins" published by the McGraw-Hill Book Company (1980).

For example, the thickeners that may be used may be thickening systems based on associative- polymers that are well known to those skilled in the art, for example, of non-ionic, anionic, cationic or amphoteric nature.

As used herein, the term "associative polymers" means hydrophilic polymers capable, in an aqueous medium, of reversibly associating with each other or with other molecules. Their chemical structure may, for example, comprise at least one hydrophilic region and at least one hydrophobic region. As used herein, the term "hydrophobic group" means a radical or polymer comprising a saturated or unsaturated, linear or branched, hydrocarbon-based chain comprising at least ten carbon atoms, for example, from 10 to 30 carbon atoms, further, for example, from 12 to 30 carbon atoms and even further, for example, from 18 to 30 carbon atoms. For example, the hydrocarbon-based group may originate from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

According to one embodiment, the composition of the disclosure may comprise at least one associative polymer chosen from associative polyurethanes, which are, for example, cationic or nonionic, associative cellulose derivatives, further, for example, cationic or nonionic, associative vinyllactams, associative unsaturated polyacids, associative aminoplast-ethers, associative polymers or copolymers comprising at least one ethylenically unsaturated monomer comprising a sulfonic group, alone or as mixtures.

Among the associative thickening polymers that may be mentioned include, for example, associative polyurethane derivatives, for instance those obtained by polymerization of:
from 20% to 70% by weight of an α,β-monoethylenically unsaturated carboxylic acid,
from 20% to 80% by weight of a non-surfactant α,β-monoethylenically unsaturated monomer, which is different from the previous monomer,
from 0.5% to 60% by weight of a nonionic monourethane, which is the product of reaction of a monohydroxylated surfactant with a monoethylenically unsaturated monoisocyanate.

Such polymers are described in European Patent No. EP 173 109, for example, in Example 3. For example, this polymer is a methacrylic acid/methyl acrylate/dimethyl meta-isopropenyl benzyl isocyanate terpolymer of ethoxylated behenyl alcohol (40 EO) as an aqueous 25% dispersion. This product is sold under the reference Viscophobe DB1000 by the company Amerchol.

Cationic associative polyurethanes, the family of which has been described in French Patent Application No. FR 0 009 609, are also suitable for use. It may be represented, for example, by the general formula (A) below:

R—X—(P)$_n$-[L-(Y)$_m$]$_r$-L'-(P')$_p$-X'—R'  (A)

wherein:
R and R', which may be identical or different, are each chosen from hydrophobic groups or hydrogen atoms;
X and X', which may be identical or different, are each chosen from groups comprising an amine function optionally bearing a hydrophobic group, or alternatively a group L";
L, L' and L", which may be identical or different, are each chosen from groups derived from a diisocyanate;
P and P', which may be identical or different, are each chosen from groups comprising an amine function optionally bearing a hydrophobic group;
Y is chosen from a hydrophilic group;
r is an integer ranging from 1 to 100, for example, from 1 to 50 and further, for example, from 1 to 25;
n, m and p, which may be identical or different, each range from 0 to 1000;
the molecule comprising at least one protonated or quaternized amine function and at least one hydrophobic group.

In one embodiment of these polyurethanes, the only hydrophobic groups are the groups R and R' at the chain ends.

According to one embodiment, the associative polyurethane corresponds to formula (A) wherein R and R' are independently chosen from hydrophobic groups; X and X' are chosen from L"; n and p, which may be identical or different, range from 1 to 1000, and L, L', L", P, P', Y and m have the meaning given as in formula (A) above.

According to another embodiment of the disclosure, the associative polyurethane corresponds to formula (A) wherein R and R' are each chosen from hydrophobic groups, X and X' are chosen from L", n and p are 0, and L, L', L", Y and m have the meaning as in formula (A) above.

The fact that n and p are 0 means that these polymers do not comprise units derived from a monomer comprising an amine function, incorporated into the polymer during the polycondensation. The protonated amine functions of these polyurethanes result from the hydrolysis of excess isocyanate functions, at the chain end, followed by alkylation of the primary amine functions formed with alkylating agents comprising a hydrophobic group, i.e. compounds of the type RQ or R'Q, wherein R and R' are as defined above and Q is chosen from a leaving group such as a halide, a sulfate, etc.

In another embodiment of the disclosure, the associative polyurethane corresponds to formula (A) wherein R and R' are each chosen from hydrophobic groups; X and X' are each chosen from groups comprising quaternary amines; n and p are zero and L, L', Y and m have the meaning indicated in formula (A) above.

The number-average molecular mass of the cationic associative polyurethanes may for example, range from 400 to 500 000, for example, from 1000 to 400 000 and, further, for example, from 1000 to 300 000 g/mol.

When X and/or X' are each chosen from groups comprising tertiary or quaternary amines, X and/or X', which may be identical or different, may be chosen from:

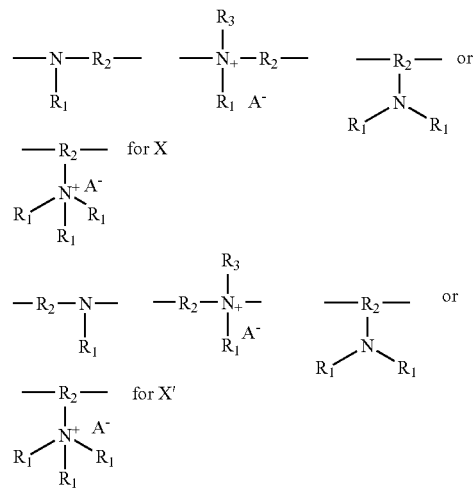

wherein:
R$_2$ is chosen from a linear or branched alkylene radical comprising from 1 to 20 carbon atoms, optionally comprising a saturated or unsaturated ring, or an arylene radical, at least one of the carbon atoms possibly being replaced with a hetero atom chosen from N, S, O and P;
R$_1$ and R$_3$, which may be identical or different, are chosen from linear or branched C$_1$-C$_{30}$ alkyl or alkenyl radicals or aryl radicals, at least one of the carbon atoms optionally being replaced with a hetero atom chosen from N, S, O and P;

A⁻ is a physiologically acceptable counterion.

The groups L, L' and L" represent a group of formula:

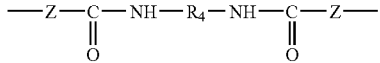

wherein:

Z is chosen from —O—, —S— or —NH—; and

R₄ is chosen from linear or branched alkylene radicals comprising from 1 to 20 carbon atoms, optionally comprising a saturated or unsaturated ring, or an arylene radical, at least one of the carbon atoms optionally being replaced with a hetero atom chosen from N, S, O and P.

The groups P and P' comprising an amine function may be chosen from:

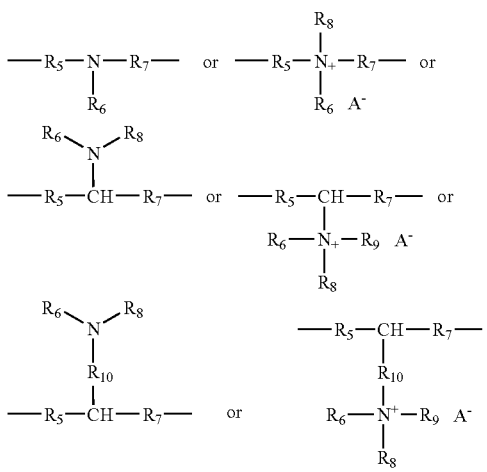

wherein:

R₅ and R₇ have the same meanings as R₂ defined above;

R₆, R₈ and R₉ have the same meanings as R₁ and R₃ defined above;

R₁₀ is chosen from a linear or branched, optionally unsaturated alkylene group possibly comprising at least one hetero atoms chosen from N, O, S and P; and A⁻ is a cosmetically acceptable counterion.

As regards the meaning of Y, as used herein, the term "hydrophilic group" means a polymeric or non-polymeric water-soluble group. By way of example, when it is not a polymer, mention may be made of ethylene glycol, diethylene glycol and propylene glycol. When it is a hydrophilic polymer, in accordance with one embodiment, mention may be made, for example, of polyethers, sulfonated polyesters, sulfonated polyamides or a mixture of these polymers. The hydrophilic compound is, for example, a polyether and, further, for example, a poly(ethylene oxide) or poly(propylene oxide).

The associative polyurethanes of formula (A) are formed from diisocyanates and from various compounds with functions comprising a labile hydrogen. The functions comprising a labile hydrogen may be, for example, alcohol, primary or secondary amine or thiol functions, giving, after reaction with the diisocyanate functions, polyurethanes, polyureas and polythioureas, respectively. The expression "polyurethanes" which can be used according to the present disclosure encompasses these three types of polymer, namely polyurethanes per se, polyureas and polythioureas, and also copolymers thereof.

A first type of compound included in the preparation of the polyurethane of formula (A) is a compound comprising at least one unit comprising an amine function. This compound may be multifunctional, but the compound may be, for example, difunctional, that is to say that, according to one embodiment, this compound comprises two labile hydrogen atoms borne, for example, by a hydroxyl, primary amine, secondary amine or thiol function. A mixture of multifunctional and difunctional compounds wherein the percentage of multifunctional compounds is low may also be used.

As mentioned above, this compound may comprise more than one unit comprising an amine function. In this case, it is a polymer bearing a repetition of the unit comprising an amine function.

Compounds of this type may be represented by one of the following formulae:

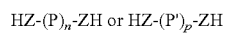

wherein Z, P, P', n and p are as defined above.

Non-limiting examples of compounds comprising an amine function that may be mentioned include N-methyidi-ethanolamine, N-tert-butyidiethanolamine and N-sulfoeth-yldi-ethanolamine.

The second compound included in the preparation of the polyurethane of formula (A) is a diisocyanate corresponding to the formula O═C═N—R₄—N═C═O, wherein R₄ is as defined above.

Non-limiting mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound included in the preparation of the polyurethane of formula (A) is a hydrophobic compound intended to form the terminal hydrophobic groups of the polymer of formula (A).

This compound consists of a hydrophobic group and of a function comprising a labile hydrogen, for example a hydroxyl, primary or secondary amine, or thiol function.

By way of example, this compound may be a fatty alcohol such as stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (A) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, wherein R and R' are as defined above and Q is chosen from a leaving group such as a halide, a sulfate, etc.

The cationic associative polyurethane may also comprise a hydrophilic block. This block is provided by a fourth type of compound involved in the preparation of the polymer. This compound may be multifunctional. It is, for example, difunctional. It is also possible to have a mixture wherein the percentage of multifunctional compound is low.

The functions comprising a labile hydrogen are alcohol, primary or secondary amine or thiol functions. This compound may be a polymer terminated at the chain ends with one of these functions comprising a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers.

The hydrophilic compound may be, for example, a polyether and further, for example, a poly(ethylene oxide) or poly(propylene oxide).

The hydrophilic group termed Y in formula (A) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group may be used.

The associative polyurethane derivatives of the disclosure may also be nonionic polyurethane polyethers. For example, the said polymers comprise in their chain both hydrophilic blocks usually of polyoxyethylenated nature, and hydrophobic blocks that may be aliphatic chains alone and/or cycloaliphatic and/or aromatic chains.

For example, these polyurethane polyethers comprise at least two hydrocarbon-based lipophilic chains, comprising from 6 to 30 carbon atoms, separated by a hydrophilic block, the hydrocarbon-based chains possibly being pendent chains or chains at the end of a hydrophilic block. For example, it is possible for at least one pendent chains to be provided. In addition, the polymer may comprise a hydrocarbon-based chain at one or both ends of a hydrophilic block.

The polyurethane polyethers may be multiblock, for example, in triblock form. The hydrophobic blocks may be at each end of the chain (for example: triblock copolymer comprising a hydrophilic central block) or distributed both at the ends and in the chain (for example multiblock copolymer). These same polymers may also be graft polymers or starburst polymers.

The fatty-chain nonionic polyurethane polyethers may be triblock copolymers whose hydrophilic block is a polyoxyethylenated chain comprising from 50 to 1000 oxyethylenated groups.

The nonionic polyurethane polyethers comprise a urethane bond between the hydrophilic blocks, whence arises the name.

By extension, also featured among the hydrophobic-chain nonionic polyurethane polyethers are those whose hydrophilic blocks are linked to the hydrophobic blocks via other chemical bonds.

As examples of hydrophobic-chain nonionic polyurethane polyethers that may be used in the disclosure, use may also be made of Rheolate 205® comprising a urea function, sold by the company Rheox, or alternatively Rheolates® 208, 204 or 212 or Acrysol RM 184®.

For example, mention may also be made of the product Elfacos T210® comprising a $C_{12-14}$ alkyl chain and the product Elfacos T212® comprising a $C_{18}$ alkyl chain, from Akzo.

The product DW 1206B® from Rohm & Haas comprising a $C_{20}$ alkyl chain and a urethane linkage, sold at a solids content of 20% in water, may also be used.

It is also possible to use solutions or dispersions of these polymers, for example, in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used described above may also be chosen from those described in the article by G. Fonnum, J. Bakke and Fk. Hansen—Colloid Polym. Sci. 271, 380-389 (1993).

In one embodiment, a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate may be used.

Such polyurethane polyethers are sold by the company Rohm & Haas under the names Aculyn 46® and Aculyn 44® [Aculyn 46® is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol comprising 150 or 180 mol of ethylene oxide, of decyl alcohol and of methylenebis(4-cyclohexylisocyanate) (SMDI), at 35% by weight in a mixture of propylene glycol (39%) and water (26%)].

The composition may also comprise polymers derived from associative celluloses, such as:

quaternized cationic celluloses modified with groups comprising at least one hydrophobic chain, such as alkyl, arylalkyl or alkylaryl groups comprising at least 8 carbon atoms, or mixtures thereof, quaternized cationic hydroxyethylcelluloses modified with groups comprising at least one hydrophobic chain, such as alkyl, arylalkyl or alkylaryl groups comprising at least 8 carbon atoms, or mixtures thereof.

The alkyl radicals borne by the above quaternized celluloses or hydroxyethylcelluloses may, for example, comprise from 8 to 30 carbon atoms. The aryl radicals may, for example, be chosen from phenyl, benzyl, naphthyl or anthryl groups.

Examples of quaternized alkylhydroxyethylcelluloses comprising $C_8$-$C_{30}$ hydrophobic chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

nonionic cellulose derivatives such as hydroxyethyl celluloses modified with groups comprising at least one hydrophobic chain, such as alkyl, arylalkyl or alkylaryl groups, or mixtures thereof, and wherein the alkyl groups are of $C_8$-$C_{22}$, for instance the product Natrosol Plus Grade 330 CS® ($C_{16}$ alkyls) sold by the company Aqualon, or the product Bermocoll EHM 100® sold by the company Berol Nobel, cellulose derivatives modified with polyalkylene glycol alkylphenol ether groups, such as the product Amercell Polymer HM-1500® sold by the company Amerchol.

As regards the associative polyvinyllactams, examples that may be mentioned include the polymers described, for example, in French Patent No. FR 0 101 106. The said polymers are cationic polymers and comprise:

a) at least one monomer of vinyllactam or alkylvinyllactam type;
b) at least one monomer of structure (a) or (b) below:

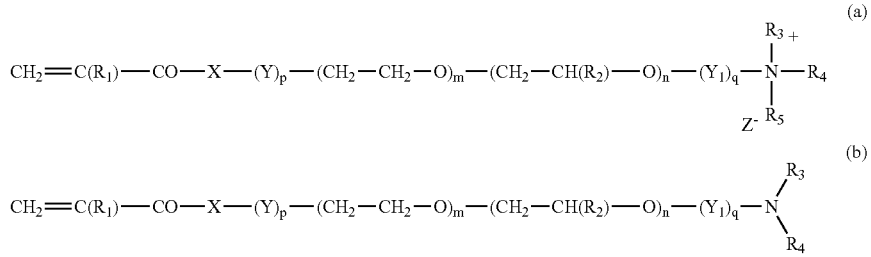

wherein:

X is chosen from oxygen atoms and $NR_6$ radicals, $R_1$ and $R_6$, which may be identical or different, are each chosen from a hydrogen atom or linear or branched $C_1$-$C_5$ alkyl radicals, $R_2$ is chosen from linear and branched $C_1$-$C_4$ alkyl radicals, $R_3$, $R_4$ and $R_5$, which may be identical or different, are each chosen from a hydrogen atom, linear or branched $C_1$-$C_{30}$ alkyl radicals and radicals of formula (c):

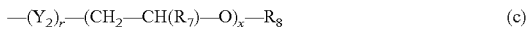

wherein Y, $Y_1$ and $Y_2$, which may be identical or different, are each chosen from linear or branched $C_2$-$C_{16}$ alkylene radicals, $R_7$ is chosen from a hydrogen atom, linear or branched $C_1$-$C_4$ alkyl radicals, and linear or branched $C_1$-$C_4$ hydroxyalkyl radicals, $R_8$ is chosen from a hydrogen atom and linear or branched $C_1$-$C_{30}$ alkyl radicals, p, q and r, which may be identical or different, are each chosen from 0 or 1.

m and n denote, which may be identical or different, are each chosen from a number ranging from 0 to 100, x is chosen from a number ranging from 1 to 100, Z is chosen from organic anions and mineral acid anions, wherein:

at least one of the substituents $R_3$, $R_4$, $R_5$ or $R_8$ is chosen from linear or branched $C_9$-$C_{30}$ alkyl radicals, if m or n is other than zero, then q is equal to 1, if m or n is equal to zero, then p or q is equal to 0.

The poly(vinyllactam)polymers may be crosslinked or non-crosslinked and may also be block polymers.

For example, the counterion $Z^-$ of the monomers of formula (b) may be chosen from halide ions, phosphate ions, the methosulfate ion and the tosylate ion.

For example, $R_3$, $R_4$ and $R_5$, which may be identical or different, are each chosen from, a hydrogen atom or linear or branched $C_1$-$C_{30}$ alkyl radicals.

Further, for example, the monomer b) is a monomer of formula (b) for which m and n are equal to zero.

The vinyllactam or alkylvinyllactam monomer may be, for example, a compound of structure (d):

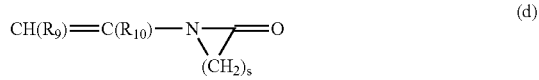

wherein:

s is chosen from an integer ranging from 3 to 6, $R_g$ is chosen from a hydrogen atom and $C_1$-$C_5$ alkyl radicals, $R_{10}$ is chosen from a hydrogen atom and $C_1$-$C_5$ alkyl radicals, wherein at least one of the radicals $R_9$ and $R_{10}$ is chosen from a hydrogen atom.

For example, the monomer (d) is vinylpyrrolidone.

The poly(vinyllactam)polymers may also comprise at least one additional monomer, for example, cationic or nonionic monomers.

For example, terpolymers according to the disclosure may comprise at least:

a) one monomer of formula (d), b) one monomer of formula (a) wherein p=1, q=0, $R_3$ and $R_4$, which may be identical or different, are chosen from a hydrogen atom or $C_1$-$C_5$ alkyl radicals and $R_5$ is chosen from $C_9$-$C_{24}$ alkyl radicals, and c) a monomer of formula (b) wherein $R_3$ and $R_4$, which may be identical or different, are chosen from a hydrogen atom or $C_1$-$C_5$ alkyl radicals.

For example, terpolymers comprising, by weight, 40% to 95% of monomer (d), 0.1% to 55% of monomer (a) and 0.25% to 50% of monomer (b) may be used. Such polymers are described in PCT Patent Application No. WO 00/68282, the content of which forms an integral part of the disclosure.

As poly(vinyllactam)polymers, vinylpyrrolidone/dimethylaminopropyl-methacrylamide/dodecyldimethyl-methacrylamidopropylammonium, tosylate terpolymers, vinyl-pyrrolidone/dimethylaminopropylmethacrylamide/cocoyl-dimethylmethacrylamidopropylammonium, tosylate terpolymers, vinylpyrrolidone/dimethyl-aminopropylmethacrylamide/lauryidimethylmethacrylamidopropylammonium, tosylate or chloride terpolymers may, for example, be used. The vinylpyrrolidone/dimethyl-aminopropylmethacrylamide/lauryldimethylmethacrylamidopropylammonium, chloride terpolymer is sold at a concentration of 20% in water by the company ISP under the name Styleze W20.

The associative polyvinyllactam derivatives of the disclosure may also be nonionic copolymers of vinylpyrrolidone and of hydrophobic monomers comprising a hydrophobic chain, among which non-limiting mention may be made, for example, of:

the products Antaron V216® or Ganex V216® (vinylpyrrolidone/hexadecene copolymer) sold by the company ISP, the products Antaron V220® or Ganex V220® (vinylpyrrolidone/eicosene copolymer) sold by the company ISP.

Among the associative unsaturated polyacid derivatives that may be mentioned are those comprising at least one hydrophilic unit of unsaturated olefinic carboxylic acid type, and at least one hydrophobic unit of unsaturated carboxylic acid ($C_{10}$-$C_{30}$) alkyl ester type.

These polymers may be, for example, chosen from those wherein the hydrophilic unit of unsaturated olefinic carboxylic acid type corresponds to the monomer of formula (e) below:

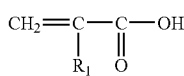  (e)

wherein $R_1$ is chosen from H, $CH_3$ and $C_2H_5$, for example, acrylic acid, methacrylic acid or ethacrylic acid units, and wherein the hydrophobic unit of the type ($C_{10}$-$C_{30}$)alkyl ester of an unsaturated carboxylic acid corresponds to the monomer of formula (f) below:

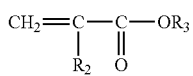  (f)

wherein formula $R_2$ is chosen from H, $CH_3$ and $C_2H_5$ (i.e. acrylate, methacrylate or ethacrylate units), for example, H (acrylate units) or $CH_3$ (methacrylate units), $R_3$ denoting a $C_{10}$-$C_{30}$, for example, $C_{12}$-$C_{22}$ alkyl radical. ($C_{10}$-$C_{30}$)Alkyl esters of unsaturated carboxylic acids comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacryiate and dodecyl methacrylate.

Anionic polymers of this type are disclosed and prepared, for example, according to U.S. Pat. Nos. 3,915,921 and 4,509,949.

In anionic associative polymers of this type, use may be made, for example, of polymers formed from a mixture of monomers comprising:

(i) essentially acrylic acid,
(ii) an ester of formula (f) described above, wherein $R_2$ is chosen from H and $CH_3$, $R_3$ is chosen from an alkyl radical comprising from 12 to 22 carbon atoms, and
(iii) a crosslinking agent, which is a well-known copolymerizable polyethylenic unsaturated monomer, for instance diallyl phthalate, allyl(meth)acrylate, divinylbenzene, (poly)ethylene glycol dimethacrylate or methylenebisacrylamide.

Among the anionic associative polymers of this type, for example, are those ranging from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those ranging from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, for example, are the products sold by the company Goodrich under the trade names Pemulen $TR_1$®, Pemulen $TR_2$® and Carbopol 1382®, and Pemulen $TR_1$®, and the product sold by the company SEPPIC under the name Coatex SX®.

Among the associative unsaturated polyacid derivatives that may also be mentioned are those comprising among their monomers an α,β-monoethylenically unsaturated carboxylic acid and an ester of an α,β-monoethylenically unsaturated carboxylic acid and of an oxyalkylenated fatty alcohol.

These compounds may also, for example, comprise as monomer an ester of an α,β-monoethylenically unsaturated carboxylic acid and of a $C_1$-$C_4$ alcohol.

An example of compounds of this type that may be mentioned is Aculyn 22® sold by the company Rohm & Haas, which is a methacrylic acid/ethyl acrylate/oxyalkylenated stearyl methacrylate terpolymer.

As regards the thickening polymers of the aminoplast-ether type, any product derived from the condensation of an aldehyde with an amine or an amide, and any structural unit formed from an aminoplast residue and from a divalent hydrocarbon-based residue linked to the aminoplast residue via an ether bond, is designated.

The polymers with an aminoplast-ether skeleton may be chosen from those comprising at least one unit of structure (g) below:

  (g)

wherein:
AMP is an aminoplast residue with alkylene units (or divalent alkyl),
R is chosen from a hydrogen atom, $C_1$-$C_4$ alkyl radicals and $C_1$-$C_4$ acyl radicals,
$RO_1$ is a divalent alkyleneoxy residue,
p is chosen from a positive integer,
the group(s) OR being linked to the alkylene units of the AMP residue.

For example, the polymers with an aminoplast-ether skeleton are chosen from those comprising at least one unit of structure (h) below:

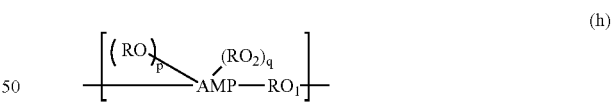  (h)

wherein:
AMP, R, $RO_1$ and p have the same meaning as above,
$RO_2$ is a group other than RO linked to AMP via a hetero atom and comprising at least two carbon atoms, and
q is a positive integer.

By further example, the polymers correspond to formulae (III) and (IIIa) below:

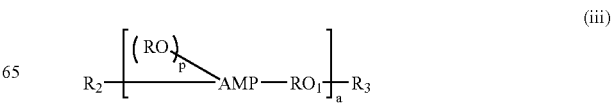  (iii)

-continued

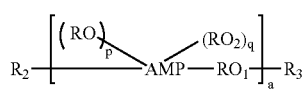
(iiia)

wherein:

AMP, R, $RO_1$, $RO_2$, p and q have the same meaning as above, $R_2$ or $R_3$, which may be identical or different, are chosen from end groups that can be chosen from a hydrogen atom, $RO_1H$, $RO_2H$, $AMP(OR)p$ or any monofunctional group such as alkyl, cycloalkyl, aryl, aralkyl, alkylaryl, alkyloxyalkyl, aryloxyalkyl or cycloalkoxyalkyl, a being a number greater than 1, for example, greater than 2.

The aminoplast residues bearing the groups OR thereof integrated into the polymers may be chosen, in a nonlimiting manner, from structures (1) to (12) below:

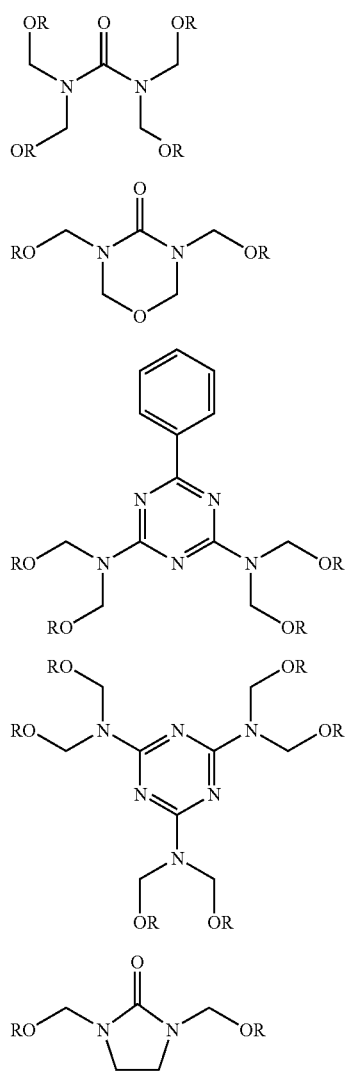

(1)

(2)

(3)

(4)

(5)

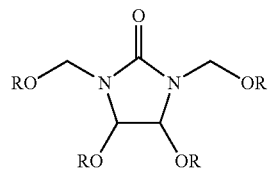

(6)

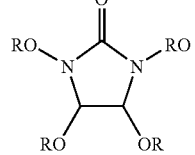

(7)

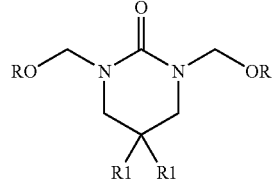

(8)

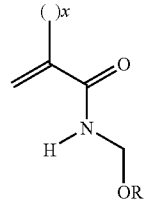

(9)

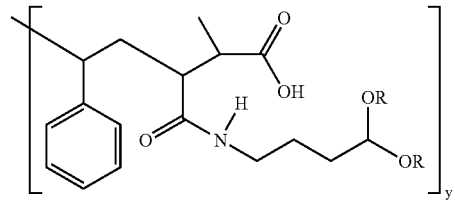

(10)

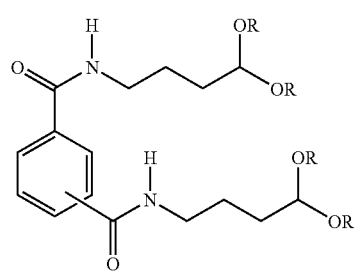

(11)

(12)

wherein:

R has the same meaning as above, $R_1$ is chosen from $C_1$-$C_4$ alkyl, y is a number at least equal to 2, x is chosen from 0 or 1.

For example, the aminoplast residue(s) bearing the groups OR thereof is (are) chosen from those of structure (13) below:

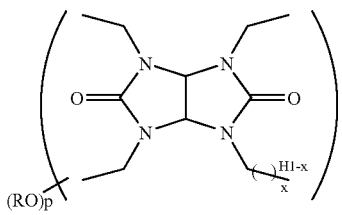

(13)

wherein R, p and x have the same meanings as above.

The divalent alkyleneoxy residues may be, for example, those corresponding to the diols of general formula (14) below:

(14), y and y', which may be identical or different, are chosen from numbers ranging from 0 to 1000, t and w, which may be identical or different, are chosen from numbers ranging from 0 to 10, Z, Z', $Z_2$ and $Z_3$, which may be identical or different, are chosen from $C_2$-$C_4$ alkylene radicals, for example, —$CH_2$—$CH(Z_4)$- and —$CH_2$—$CH(Z_4)$-$CH_2$—, $Z_1$ is chosen from a linear or cyclic, branched or unbranched, aromatic or non-aromatic radical optionally comprising at least one hetero atom and comprising from 1 to 40 carbon atoms, $Z_4$ is chosen from a hydrogen atom, $C_1$-$C_4$ alkyl radicals, $C_1$-$C_3$ acyl radicals, wherein at least one of the radicals $Z_4$ of the radicals Z, Z', $Z_2$ and $Z_3$ is other than an acyl radical.

For example, $Z_4$ is chosen from a hydrogen atom or a methyl radical.

Further, for example, t is equal to 0 and Z, Z' and $Z_3$ are —$CH_2CH_2$—, and at least one of the groups from among y and y' is other than 0. The compounds of formula (14) are then polyethylene glycols.

The aminoplast-ether polymers of formula (g) are described in U.S. Pat. No. 5,914,373, to which reference may be made for further details.

As polymers with an aminoplast-ether skeleton of formula (g), mention may be made of the products Pure-Thix® L [PEG-180/Octoxynol-40/TMMG Copolymer (INCI name)], Pure-Thix M® [PEG-180/Laureth-50/TMMG Copolymer (INCI name)] and Pure-Thix® HH [Polyether-1 (INCI name)]; Pure-Thix TX-1442® [PEG-18/dodoxynol-5/PEG-25 tristyrylphenol/tetramethoxy methyl glycoluril copolymer], sold by the company Süd-Chemie.

The thickening polymers included as ingredient in the composition according to the disclosure may also be chosen from associative polymers comprising at least one ethylenically unsaturated monomer comprising a sulfonic group, in free or partially or totally neutralized form and comprising at least one hydrophobic portion.

For example, the said polymers are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine and basic amino acids, for instance arginine and lysine, and mixtures of these compounds.

These associative polymers may or may not be crosslinked, and are for example, crosslinked polymers. In this case, the crosslinking agents are derived from at least one monomer comprising at least two ethylenic unsaturations (carbon-carbon double bond).

The crosslinking monomers comprising at least two ethylenic unsaturations are chosen, for example, from diallyl ether, triallyl cyanurate, diallyl maleate, allyl(meth)acrylate, dipropylene glycol diallyl ether, polyglycol diallyl ethers, triethylene glycol divinyl ether, hydroquinone diallyl ether, tetraallyloxethanoyl, diethylene glycol di(meth)acrylate or tetraethylene glycol di(meth)acrylate, triallylamine, tetraallylethylenediamine, trimethylolpropane diallyl ether, trimethylolpropane triacrylate, methylenebis(meth)acrylamide or divinylbenzene, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate may be used, for example. The degree of crosslinking may range from 0.01 mol % to 10 mol % relative to the polymer.

The ethylenically unsaturated monomers comprising a sulfonic group may be chosen from, for example, vinylsulfonic acid, styrenesulfonic acid, (meth)acrylamido($C_1$-$C_{22}$)alkylsulfonic acids, and N—($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, may be used, for example.

2-Acrylamido-2-methylpropanesulfonic acid (AMPS), and also partially or totally neutralized forms thereof, may be used, for example.

The amphiphilic polymers present in the composition according to the disclosure may also be chosen from random amphiphilic AMPS polymers modified by reaction with a $C_6$-$C_{22}$ n-monoalkylamine or di-n-alkylamine, and such as those described in PCT Patent Publication No. WO 00/31154.

The hydrophobic monomers that constitute the hydrophobic portion of the polymer may be, for example, chosen from the acrylates or acrylamides of formula (k) below:

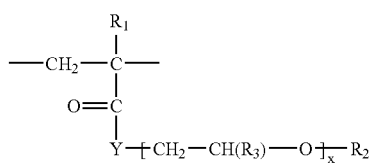

wherein $R_1$ and $R_3$, which may be identical or different, are chosen from a hydrogen atom and linear or branched $C_1$-$C_6$ alkyl radicals (for example, methyl); Y is chosen from O and NH; $R_2$ is chosen from a hydrophobic hydrocarbon-based radical as defined previously; x is chosen from a number of moles of alkylene oxide and ranges from 0 to 100.

The radical $R_2$ may be, for example, chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, examples are linear alkyl radicals, further, for example, the n-dodecyl radical.

According to one embodiment of the disclosure, the monomer of formula (k) comprises at least one alkylene oxide unit (x≧1), for example, a polyoxyalkylenated chain. The polyoxyalkylenated chain, for example, consists of ethylene oxide units and/or of propylene oxide units and further, for example, consists of ethylene oxide units. The number of oxyalkylene units generally ranges from 3 to 100, for example, from 3 to 50 and further, for example, from 7 to 25.

The copolymers may also contain other ethylenically unsaturated hydrophilic monomers, chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described in European Patent No, EP 750 899 and U.S. Pat. No. 5,089,578 and in the following publications from Yotaro Morishima: "Self-assembling amphiphilic polyelectrolytes and their nanostructures—Chinese Journal of Polymer Science Vol. 18, No. 40, (2000), 323-336"; "Micelle formation of random copolymers of sodium, 2-(acrylamido)-2-methylpropanesulfonate and a nonionic surfactant macromonomer in water as studied by fluorescence and dynamic light scattering—Macromolecules 2000, Vol. 33, No. 10-3694-3704"; "Solution properties of micelle networks formed by nonionic moieties covalently bound to a polyelectrolyte: salt effects on rheological behaviour—Langmuir, 2000, Vol. 16, No. 12, 5324-5332"; "Stimuli responsive amphiphilic copolymers of sodium, 2-(acrylamido)-2-methylpropanesulfonate and associative macromonomers—Polym. Preprint, Div. Polym. Chem. 1999, 40(2), 220-221".

The distribution of the monomers in the copolymer may be in random or block form.

Among the polymers of this type, non-limiting mention may be made of:

crosslinked or non-crosslinked, neutralized or non-neutralized copolymers comprising from 15% to 60% by weight of AMPS units and from 40% to 85% by weight of ($C_8$-$C_{16}$)alkyl(meth)acrylamide units or of ($C_8$-$C_{16}$) alkyl(meth)acrylate units, relative to the polymer, such as those described in European Patent Application No. EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578;

copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made, for example, of the copolymers consisting of AMPS units of formula (I) below:

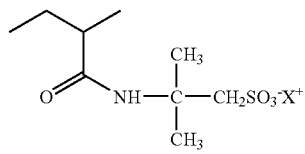

wherein $X^+$ has the same definition as previously, and of units of formula (I) below:

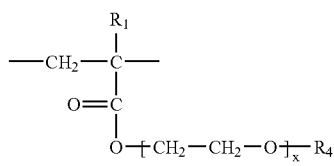

wherein x is chosen from an integer ranging from 3 to 100, for example, from 5 to 80 and further, for example, from 7 to 25; $R_1$ has the same meaning as that given above in formula (I) and $R_4$ is chosen from a linear or branched $C_6$-$C_{22}$, for example, $C_{10}$-$C_{22}$ alkyl.

The polymers may be, for example, those wherein x is equal to 25, $R_1$ is chosen from methyl and $R_4$ is chosen from n-dodecyl; they are described in the Morishima articles mentioned above.

For example, the polymers for which $X^+$ is chosen from sodium, or ammonium, may be used.

Polymers of the Genapol® range from the company Hoechst/Clariant may be used in the composition according to the disclosure.

The concentration of associative or non-associative thickening polymer(s) present in the composition according to the disclosure may range from 0.01% to 10% by weight, for example, from 0.1% to 5% by weight, relative to the weight of the composition, and further, for example, from 0.5% to 5% by weight, relative to the weight of the composition.

According to one embodiment, the composition can comprise at least one surfactant and/or thickening polymer.

Needless to say, a person skilled in the art will take care to select this or these optional additional compound(s) such that the advantageous properties intrinsically associated with the composition in accordance with the disclosure are not, or are not substantially, adversely affected by the envisaged addition(s).

The composition according to the disclosure may be in various forms, such as in the form of liquids, shampoos, creams or gels, or in any other suitable form.

In one embodiment, the form is a dyeing and/or lightening shampoo comprising, in a cosmetically acceptable aqueous medium, at least one direct dye as defined above, and at least one surfactant, which may be nonionic.

The nonionic surfactants may be chosen from alkylpolyglucosides.

It is not excluded, for the composition to comprise at least one oxidizing agent chosen, for example, from hydrogen peroxide, urea peroxide, alkali metal bromates, persalts such as perborates and persulfates, and enzymes such as peroxidases and two-electron or four-electron oxidoreductases. For example, hydrogen peroxide may be used.

Another subject of the disclosure consists of a process for treating keratin fibers, for example, human keratin fibers.

According to one embodiment, a composition of the disclosure is applied to said wet or dry fibers, for a sufficient time, after which the fibers are rinsed, optionally washed with shampoo, rinsed again and dried, or the resulting fibers are left to dry. This embodiment may be used for compositions of any type, whether or not they comprise an oxidizing agent and/or a direct dye and/or an oxidation base optionally combined with a coupler.

According to another embodiment, a composition as defined is applied to the said wet or dry fibers without final rinsing. This embodiment may be suitable for compositions not comprising an oxidation dye (oxidation base and optionally coupler) or an oxidizing agent.

The application time is usually sufficient to develop the desired coloration and/or lightening.

As a guide, the application time for the composition may range from 5 to 60 minutes, for example, from 15 to 60 minutes.

Moreover, in one embodiment, the temperature at which the process according to the disclosure is performed is generally ranging from room temperature (15 to 25° C.) to 60° C., for example, from 15 to 45° C.

When the composition comprises an oxidizing agent, the process according to the disclosure may comprise a preliminary step that consists in separately storing, on the one hand, a composition comprising, in a cosmetically acceptable medium, at least one direct dye of formula (I) or (I'), optionally at least one additional direct dye and/or optionally at least one oxidation base optionally combined with at least one coupler, and, on the other hand, a composition comprising, in a cosmetically acceptable medium, at least one oxidizing agent, and then in mixing them together at the time of use. Once this has been performed, the process according to the disclosure may be carried out in accordance with the indications mentioned previously.

Another subject of the disclosure is a multi-compartment device, comprising at least one compartment comprising a composition comprising at least one direct dye of formula (I) or (I'), and at least one other compartment comprising a composition comprising at least one oxidizing agent. This device may be equipped with a means for applying the desired mixture to the hair, such as the devices described in French Patent Application FR-2 586 913.

It should be noted that the in the case where the composition comprises at least one additional direct dye and/or at least one oxidation base optionally combined with at least one coupler, according to one embodiment, this or these compounds(s) is (are) in the first compartment of the device previously described. According to another embodiment, the additional direct dye and/or the oxidation base/coupler are stored in a third compartment.

It would not be excluded to have another embodiment combining the two previous embodiments, wherein the additional direct dye and/or the oxidation base and optionally the coupler would be partly in the first compartment, with the direct compound of formulae (I) or (I'), and partly in a third compartment.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contain certain errors necessarily resulting from the standard deviation found in their respective testing measurements.

The embodiments disclosed herein are illustrated in greater detail by the examples described below.

EXAMPLE 1

The following composition was prepared:

| Compound (A) | $10^{-3}$ mol % |
|---|---|
| Distilled water | qs 100 |

Compound (A) has the following structure:

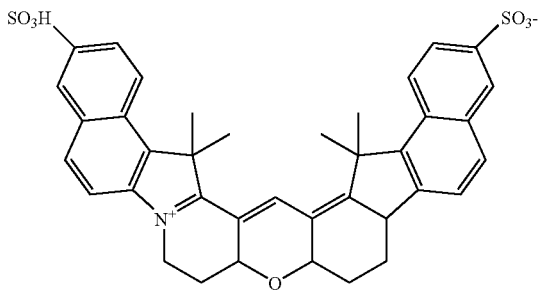

Internal salt of dibenzo[e,e']pyrano[3",2":3,4;5",6":3',4'] dipyrido[1,2-a:1',2'-a']di-indol-7-ium, 8,9,11,12,20,22-hexahydro-20,20,22,22-tetramethyl-3,17-disulfo The composition was applied to natural grey hair for 20 minutes at room temperature. The bath ratio was set at 5. After dyeing, the locks were rinsed and dried.

The violet color obtained was shampoo-fast.

The composition was stable on storage.

EXAMPLE 2

The following composition was prepared:

| Compound (B) | $10^{-3}$ mol % |
|---|---|
| Distilled water | qs 100 |

Compound (B) has the following structure:

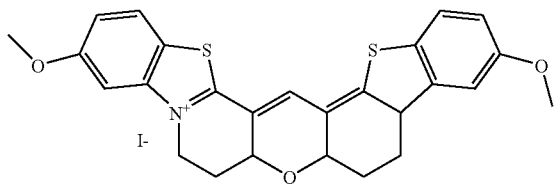

6H,10H-Pyrano[3",2":3,4;5",6":3',4']dipyrido[2,1-b:2',1'-b']bisbenzothiazol-5-ium, 7,7a,8a,9-tetrahydro-3,13-dimethoxy, iodide The composition was applied to natural grey hair for 20 minutes at room temperature. The bath ratio was set at 5. After dyeing, the locks were rinsed and dried.

The blue color obtained was shampoo-fast.

The composition was stable on storage.

EXAMPLE 3

The following compositions were prepared:

| | |
|---|---|
| Methinic dyes of formula (A), (B) or (C) | $10^{-3}$ mol % |
| Hydroxyethylcellulose sold by Aqualon under the name Natrosol250MR | 0.384% |
| Mixture of methyl, ethyl, propyl, butyl of p-hydroxybenzoates sold by NIPA under the name NIPA ester 82121 | 0.032% |
| Alkyl(C8/C10 50/50)polyglucoside sold by SEPPIC under the name Oramix CG110 | 5% |
| Alcool benzylic alcohol | 4% |
| Propyleneglycol (8OE) | 6% |
| Demin water qsp | 100 |

The compounds (A) and (B) are as above defined.

The composition containing A was applied on natural hair with 90% of white hair. The bath ratio and the application temperature and time are respectively 1, 33° C. and 30 minutes. The hair was then rinced, washed and dried. The hair was dyed in an esthetic violet. The color was resistant to shampoo and the composition before used was stable.

The composition containing the B compound was applied on hair according to the process disclosed for the composition containing A above. The hair was then dyed in red. The color was resistant to shampoo and the composition before use was stable.

The compound (C) has the following formula:

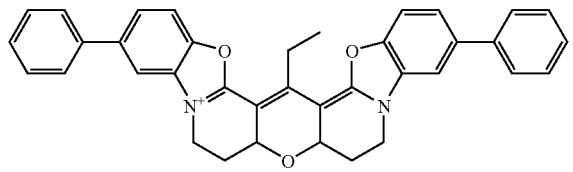

de 6H,10H-Pyrano[3",2":3,4;5",6":3',4']dipyrido[2,1-b:2',1'-b']bisbenzoxazol-5-ium, 17-ethyl-7,7a,8a,9-tetrahydro-3,13-diphenyl bromide The composition containing C was applied as disclosed for the composition containing A above. The hair was then dyed in orange. The color was resistant to shampoo and the composition before use was stable.

What is claimed is:

1. A composition for dyeing human keratin fibers comprising, in a cosmetically acceptable medium comprising water or a mixture of water and at least one organic solvent, at least one direct dye that is soluble in said medium, of formula (I) or (I'):

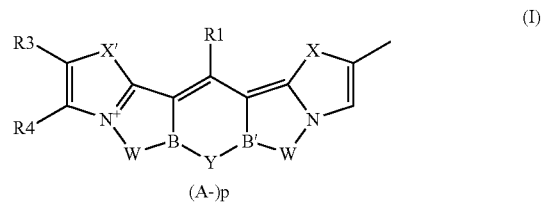

(I)

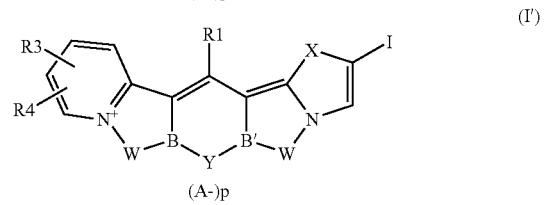

(I')

wherein:

R1 is chosen from:
  hydrogen atoms,
  linear, branched or cyclic alkyl radicals comprising from 1 to 22 carbon atoms, optionally substituted with at least one group chosen from
    hydroxyl,
    linear or branched $C_1$-$C_6$ alkoxy,
    $C_1$-$C_6$ cycloalkoxy, and
    phenyl, optionally substituted with at least one carboxyl group,
  $C_6$-$C_{30}$ aryl radicals, and
  amino radicals substituted with at least one radical chosen from linear or branched $C_1$-$C_6$ alkyls or hydroxyalkyls;

R3, R4, R5 and R6, which may be identical or different, are each chosen from:
  hydrogen atoms;
  linear or branched alkyl radicals comprising from 1 to 22 carbon atoms, optionally substituted with at least one hydroxyl radicals;
  halogen atoms;
  carboxyl radicals; and
  sulfo radicals;
or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle; wherein each aliphatic or aromatic ring or heterocycle are optionally substituted with at least one substituent chosen from:
  halogen atoms,
  $C_1$-$C_6$ alkoxy radicals,
  carboxyl radicals,
  sulfo radicals and
  $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group;

B and B', which may be identical or different, are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, ($C_6$-$C_{30}$)aryloxy($C_1$-$C_6$) alkyls or ($C_1$-$C_4$)alkyl ($C_6$-$C_{30}$)arylaminos;

X and X', which may be identical or different, are each chosen from O, S, N, NR'7, Se and CR'8R'9;

Y is chosen from O, S, N, Se, NR7, CO and CR8R9;

R8 and R9, which may be identical or different, are each chosen from
   hydrogen atoms; and
   linear or branched $C_1$-$C_{22}$ alkyl radicals optionally substituted with at least one group chosen from
      hydroxyls,
      $C_1$-$C_{10}$ mono- or dialkylaminos,
      $C_1$-$C_{10}$ mono- or dihydroxyalkylaminos,
      $C_{10}$-$C_{30}$ aryls,
      $C_{10}$-$C_{30}$ aryloxys and
      ($C_2$-$C_{10}$)acylaminos;

R7 is chosen from
   hydrogen atoms,
   linear or branched $C_1$-$C_{10}$ alkyl radicals,
   $C_6$-$C_{30}$ aryl radicals,
   amino radicals bearing at least one $C_6$-$C_{30}$ aryl radical optionally substituted with at least one substituent chosen from
      $C_1$-$C_6$ alkyl radicals
      carboxyl radicals,
      ($C_1$-$C_4$)alkyl($C_6$-$C_{30}$)arylsulfonyl radicals,
      $C_2$-$C_{10}$ acyl radicals,
      tri($C_1$-$C_4$)alkylamino($C_1$-$C_4$)alkylcarbonyl radicals, and
      aminothiocarbonyl groups;

Z and
N=Z,
   wherein Z is chosen from an optionally fused 5- or 6-membered heterocycle comprising from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and ($C_1$-$C_4$)alkoxycarbonyl($C_1$-$C_6$)alkyl radicals;

p is an number ranging from 0 to 1;

A⁻ is chosen from organic anions and mineral anions, or a mixture of anions; and wherein the content of the at least one direct dye of formula (I) or (I') ranges from 0.01 to 20% by weight, relative to the total weight of the composition.

2. A composition according to claim 1, wherein the radical R1 is chosen from hydrogen atoms and unsubstituted linear or branched $C_1$-$C_{16}$ alkyl radicals.

3. A composition according to claim 1, wherein Y is chosen from O, N, NR7 and CO.

4. A composition according to claim 1, wherein X and X', which may be identical or different, are each chosen from sulfur atoms, oxygen atoms or NR'7 wherein R'7 is chosen from $C_1$-$C_4$ alkyl radicals.

5. A composition according to claim 1, wherein X and X' are identical.

6. A composition according to claim 1, wherein W is an ethylene radical.

7. A composition according to claim 1, wherein B and B', which may be identical or different, are each chosen from carbon atoms or CH groups.

8. A composition according to claim 1, wherein R3 and R4 and/or R5 and R6 together with the carbon atoms to which each is attached, form 6- to 30-membered aliphatic or aromatic rings or heterocycles, fused to an identical or different 6- to 30-membered aromatic ring or heterocycle; wherein each aliphatic or aromatic ring or heterocycle is optionally substituted with at least one substituent chosen from
   halogen atoms,
   $C_1$-$C_6$ alkoxy radicals,
   carboxyl radicals,
   sulfo radical and
   $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group.

9. A composition according to claim 1, wherein the mineral anion is chosen from halides, sulfates, bisulfates, nitrates, phosphates, hydrogen phosphates, dihydrogen phosphates, carbonates and bicarbonates; and wherein the organic anion is chosen from anions originating from salts of saturated or unsaturated, aromatic or non-aromatic sulfonic, sulfuric, mono- or polycarboxylic acids, optionally substituted with at least one hydroxyl or amino radicals or halogen atoms.

10. A composition according to claim 9, wherein the anion is chosen from chloride, iodide, sulfate, methosulfate and ethosulfate.

11. A composition according to claim 1, wherein the at least one direct dye is chosen from:

Benzimidazo[2,1-f]benzimidazo[1',2':1,2]pyrido[4,3-b][1,6]naphthyridinium, 2,3,13,14-tetrachloro-16,18-diethyl-6,7,7a,8,8a,9,10,16-octahydro8-[(4-methylphenyl) amino], iodide 6H-Benzothiazolo[2,3-f]benzothiazolo[3',2':1,2]pyrido[4,3-b][1,6]naphthyridin-5-ium, 8-(2-benzothiazolylamino)-7,7a,8,8a,9,10-hexahydro, iodide 6H-Benzothiazolo[2,3-f]benzothiazolo[3',2':1,2]pyrido[4,3-b[1,6]naphthyridin-5-ium, 7,7a,8,8a,9,10-hexahydro-8-[[(trimethylammonio)acetyl]amino]-, chloride iodide 6H-Benzothiazolo[2,3-f]benzothiazolo[3',2':1,2]pyrido[4,3-b][1,6]naphthyridin-5-ium, 7,7a,8,8a,9,10-hexahydro-8-(4-oxo-2-thioxo-3-thiazolidinyl), iodide 6H-Benzothiazolo[2,3-f]benzothiazolo[3',2':1,2]pyrido[4,3-b][1,6]naphthyridin-5-ium, 7,7a,8,8a,9,10-hexahydro-8-[[(4-methylphenyl)sulfonyl]amino], iodide 6H-Benzothiazolo[2,3-f]benzothiazolo[3',2':1,2]pyrido[4,3-b][1,6]naphthyridin-5-ium, 8-[(1,1-dioxido-1,2-benzisothiazol-3-yl)amino]-7,7a,8,8a,9,10-hexahydro, iodide 6H-Pyrano[3",2":3,4;5",6":3',4']dipyrido[1,2-a:1',2'-a'] bisbenzimidazolium, 2,3,13,14-tetrachloro-16,18-diethyl-7,7a,8,8a,9,10,16-hexahydro, trifluoroacetate 6H,10H-Pyrano[3",2":3,4;5",6":3',4']dipyrido[2,1-b:2',1'-b']bisbenzoxazol-5-ium, 17-ethyl-7,7a,8,8a,9-tetrahydro-3,13-diphenyl, bromide 6H,10H-Pyrano[3",2":3,4;5",6":3',4']dipyrido[2,1-b:2',1'-b']bisbenzothiazol-5-ium, 7,7a,8a,9-tetrahydro-3,13-dimethoxy, iodide 6H,10H-Pyrano[3",2":3,4;5",6":3',4']dipyrido[2,1-b:2',1'-b']bisbenzothiazol-5-ium, 17-ethyl-7,7a,8a,9-tetrahydro, bromide 6H,10H-Pyrano[3",2":3,4;5",6":3',4']dipyrido[2,1-b:2',1'-b']bisbenzothiazol-5-ium, 7,7a,8a,9-tetrahydro, iodide 6H-Benzoxazolo[2,3-f]benzoxazolo[3',2':1,2]pyrido[4,3-b][1,6]naphthyridin-5-ium, 8-(2-benzothiazolylamino)-7,7a,8,8a,9,10-hexahydro-3,13-diphenyl, bromide 6H-Benzothiazolo[2,3-f]benzothiazolo[3',2':1,2]pyrido[4,3-b]naphthyridin-5-ium, 8-(2-benzothiazolylamino)-7,7a,8,8a,9,10-hexahydro, bromide 6H-Benzothiazolo[2,3-f]benzothiazolo[3',2':1,2]pyrido[4,3-b][1,6]naphthyridin-5-ium, 8-[(aminothioxomethyl)amino]-7,7a,8,8a,9,10-hexahydro, iodide 6H-Benzimidazo[2,1-f]benzimidazo[1',2':1,2]pyrido[4,3-b][1,6]naphthyridin-5-ium, 2,3,13,14-tetrachloro-16,18-diethyl-7,7a,8,8a,9,10,16,18-octahydro-9-[(4-methylphenyl)amino], iodide 9H-Bisbenzimidazo[2',1':3,4]pyrazino[1,2-c:2',1'-f]pyrimidin-5-ium, 6,7,11,12,18,20-hexahydro-9-oxo-, chloride Internal salt of pyrano[3",2":3,4;5",6":3',4']dipyrido[1,2-a:1',2'-a']diindol-5-ium, 2-(aminomethyl)-6,7,9,10,16,18-hexahydro-16,16,18,18-tetramethyl-14-sulfo Internal salt of pyrano[3",2":3,4;5",6":3',4']dipyrido[1,2-a:1',2'-a']diindol-5-ium, 2-(carboxymethyl)-6,7,9,10,16,18-hexahydro-16,16,18,18-tetramethyl-14-sulfo Internal salt of pyrano[3",2":3,4;5",6":3',4']dipyrido[1,2-a:1',2'-a']diinodol-5-ium, 2,14-bis(carboxymethyl-6,7,9,10,16,18-hexahydro-16,16,18,18-tetramethyl Internal salt of 6H-benz[2",3"]indolizino[8",7":5,6]pyrano[3,2-a]benzo[f]quinolizin-5-ium, 14-(carboxymethyl)-7,7a,8a,9,10,16-hexahydro-16,16-dimethyl Internal salt of 6H-benz[2,3]indolizino[7,8-b]indolo[2,1-f][1,6]naphthyridin-5-ium, 8-[(4-carboxyphenyl)amino]-7,7a,8,8a,9,10,16,18-octahydro-16,16,18,18-tetramethyl Internal salt of 10H-benz[2",3"]indolizino[8",7":5',6']pyrano[3',2':3,4]pyrido[2,1-b]benzothiazol-5-ium, 2-(carboxymethyl)-6,7,7a,8a,9,18-hexahydro-18,18-dimethyl Internal salt of pyrano[3",2":3,4;5",6":3',4']dipyrido[1,2-a:1',2'-a']diindol-5-ium, 6,7,9,10,16,18-hexahydro-2-(2-hydroxyethyl)-16,16,18,18-tetramethyl-14-sulfo Internal salt of pyrano[3",2":3,4;5",6":3',4']dipyrido[1,2-a:1',2'-a']diindol-5-ium, 2-[(formylamino)methyl]-6,7,9,10,16,18-hexahydro-16,16,18,18-tetramethyl-14-sulfo Internal salt of pyrano[3",2":3,4;5",6":3',4']dipyrido[1,2-a:1',2'-a']diindol-5-ium, 2-[2-[(2-aminoethyl)amino]-2-oxoethyl]-6,7,9,10,16,18-hexahydro-16,16,18,18-tetramethyl-14-sulfo Internal salt of pyrano[3",2":3,4;5",6":3',4']dipyrido[1,2-a:1',2'-a']diindol-5-ium, 2-[2-[(2-carboxymethyl)amino]-2-oxoethyl]-6,7,9,10,16,18-hexahydro-,16,16,18,18-tetramethyl-14-sulfo Internal salt of dibenzo[e,e']pyrano[3",2":3,4;5",6":3',4']dipyrido[1,2-a:1',2'-a']diindol-7-ium, 8,9,11,12,20,22-hexahydro-20,20,22,22-tetramethyl-3,17-disulfo Salt of 7H,11H-bisnaphth[2',3':4,5]oxazolo[3,2-a:3',2'-a']pyrano[3,2-c:5,6-c']dipyridin-6-ium 7H,11H-Bisnaphth[2',3':4,5]oxazolo[3,2-a:3',2'-a']pyrano[3,2-c:5,6-c']dipyridin-6-ium, 20-ethyl-8,8a,9a,10-tetrahydro-8,10-bis(3-phenoxypropyl)-, 4-methylbenzenesulfonate Salt of 7H,11H-bisnaphth[2',3':4,5]oxazolo[3,2-a:3',2'-a']pyrano[3,2-c:5,6-c']dipyridin-6-ium, 8,8a,9a,10-tetrahydro-8,10-bis(3-phenoxypropyl)

Salt of 6H,10H-naphtho[1"",2"":4"',5"']thiazolo[3"',2"':1",2"]pyrido[3",4":-5',6']pyrano[3',2':3,4]pyrido[2,1-b]benzoxazol-5

6H,10H-Pyrano[3",2":3,4;5",6":3',4']dipyrido[2,1-b:2',1'-b']bisbenzothiazol-5-ium, 7,7a,8a,9-tetrahydro, bromide Salt of 10H-benz[2",3"]indolizino[8",7":5',6']pyrano [3',2':3,4]pyrido[2,1-b]benzothiazol-5-ium Salt of dibenzo[e,e']pyrano[3",2":3,4;5",6":3',4']dipyrido[1,2-a:1',2'-a']diindol-7

Salt of pyrano[3",2":3,4;5",6":3',4']dipyrido[1,2-a:1',2'-a']diindol-5-ium

Salt of 1H-benz[2,3]indolizino[7,8-b]indolo[2,1-f][1,6]naphthyridin-5-ium 6H,10H-Pyrano[3",2":3,4;5",6":3',4']dipyrido[2,1-b:2',1'-b']bisbenzothiazol-5-ium, 7,7a,8a,9-tetrahydro-, heptafluorobutanoate 6H-Pyrano[3",2":3,4;5",6":3',4']dipyrido[1,2-a:1',2'-a']bisbenzimidazolium, 2,3,13,14-tetrachloro-16,18-diethyl-7,7a,8a,9,10,16-hexahydro, sulfate Salt of 6H-benzothiazolo[2,3-f]benzothiazolo[3',2':1,2]pyrido[4,3-b][1,6]naphthyridin-5-ium, 8-(acetylamino)-7,7a,8,8a,9, 10-hexahydro Salt of 1H-benzimidazo[2,1-f]benzimidazo[1',2':1,2]pyrido[4,3-b][1,6]naphthyridin-5-ium Benzimidazo[2,1-f]benzimidazo[1',2':1,2]pyridol[4,3-b][1,6]naphthyridinium, 2,3,13,14-tetrachloro-16,18-diethyl-6,7,7a,8,8a,9,10,16-octahydro-8-[(4-methylphenyl)amino]-, iodide Salt of pyrano[3",2":3,4;5",6":3',4']dipyrido[1,2-a:1',2'-a']bisbenzimidazol-5-ium Salt of 6H,10H-pyrano[3",2":3,4; 5",6":3',4']dipyrido[2,1-b:2',1'-b']bisbenzothiazol-5-ium Salt of 6H-benzothiazolo[2,3-f]benzothiazolo[3',2':1,2]pyrido[4,3-b][1,6]naphthyridin-5-ium Salt of 6H,10H-pyrano[3",2":3,4;5",6":3',4']dipyrido[2,1-b:2',1'-b']bisbenzoxazol-5

Salt of 6H-benzoxazolo[2,3-f]benzoxazolo[3',2':1,2]pyrido[4,3-b][1,6]naphthyridin-5-ium Salt of 6H-benzimidazo[2,1-f]benzimidazo[1',2':1,2]pyrido[4,3-b][1,6]naphthyridin-5-ium 6H-Benzothiazolo[2,3-f]benzothiazolo[3',2':1,2]pyrido[4,3-b][1,6]naphthyridin-5-ium, 8-(acetylamino)-7,7a,8,8a,9,10-hexahydro-, dichloroiodate 6,7,11,12-Tetrahydro-9-oxo-9H-bisthiazolo[3,2-a:3',2'-a']pyrimido[6,1-c:4,3-c']dipyrazin-5-ium chloride 6,7,11,12-Tetrahydro-9-oxo-9H-bisoxazolo[3,2-a:3',2'-a']pyrimido[6,1-c:4,3-c']dipyrazin-5-ium bromide 6,7,11,12-Tetrahydro-9-oxo-9H-bisselenazolo[3,2-a:3',2'-a']pyrimido[6,1-c:4,3-c']dipyrazin-5-ium bromide.

12. A composition according to claim 1, wherein the content of the at least one direct dye of formula (I) or (I') ranges from 0.1% to 5% by weight, relative to the total weight of the composition.

13. A composition according to claim 1, comprising at least one additional direct dye chosen from non-ionic, cationic and anionic dyes.

14. A composition according to claim 13, wherein the at least one additional direct dye is chosen from nitrobenzene dyes, azo, anthraquinone, naphthoquinone or benzoquinone dyes, indigoid dyes or triarylmethane-based dyes and natural dyes, and mixtures thereof.

15. A composition according to claim 13, wherein the at least one additional direct dye is present in an amount ranging from 0.0005% to 12% by weight, relative to the total weight of the composition.

16. A composition according to claim 1, comprising at least one surfactant and/or thickening agent.

17. A composition according to claim 16, wherein the at least one surfactant is non-ionic.

18. A composition according to claim 16, wherein the at least one surfactant is present in an amount ranging from 0.01% to 50% by weight, relative to the total weight of the composition.

19. A composition according to claim 1, comprising at least one non-associative thickening polymer.

20. A composition according to claim 19, wherein the at least one non-associative thickening polymer is chosen from crosslinked acrylic acid homopolymers, crosslinked 2-acrylamido-2-methylpropanesulfonic acid homopolymers and the crosslinked acrylamide copolymers thereof, ammonium acrylate homopolymers or copolymers of ammonium acrylate and of acrylamide, nonionic guar gums, biopolysaccharide gums of microbial origin, gums originating from plant exudates, hydroxypropyl- or carboxymethyl celluloses; pectins and alginates, or mixtures thereof.

21. A composition according to claim 1, comprising at least one associative thickening polymer.

22. A composition according to claim 21, wherein the at least one associative thickening polymer is chosen from associative polyurethanes, associative cellulose derivatives, associative vinyllactams, associative unsaturated polyacids, associative aminoplast-ethers, crosslinked 2-acrylamido-2-methylpropanesulfonic acid homopolymers and crosslinked acrylamide copolymers thereof, associative polymers or copolymers comprising at least one ethylenically unsaturated monomer comprising a sulfonic group, or mixtures thereof.

23. A composition according to claim 19, wherein the content of the at least one non-associative thickening polymer is present in an amount ranging from 0.01% to 10% by weight, relative to the total weight of the composition.

24. A composition according to claim 21, wherein the content of the at least one associative thickening polymer is present in an amount ranging from 0.01% to 10% by weight, relative to the total weight of the composition.

25. A composition according to claim 1, wherein the composition is in the form of a coloring shampoo.

26. A composition according to claim 1, wherein the composition comprises at least one oxidation base optionally combined with at least one coupler.

27. A composition according to claim 26, wherein the at least one oxidation base is chosen from para-phenylenediamines, bis-phenylalkylenediamines, para-aminophenols, ortho-aminophenols and heterocyclic bases, or the addition salts thereof with an acid or with an alkaline agent.

28. A composition according to claim 27, wherein the at least one oxidation base is present in an amount ranging from 0.0005% to 12% by weight, relative to the total weight of the composition.

29. A composition according to claims 26, wherein at the at least one coupler is chosen from meta-phenylenediamines, meta-aminophenols, meta-diphenols and heterocyclic couplers, or the addition salts thereof with an acid or with an alkaline agent.

30. A composition according to claim 29, wherein the at least one coupler is present in an amount ranging from 0.0001% to 10% by weight, relative to the total weight of the dye composition.

31. A composition according to claim 1, comprising at least one adjuvant chosen from anionic, cationic, nonionic, amphoteric and zwitterionic polymers or mixtures thereof; mineral thickeners; antioxidants; penetrating agents; sequestering agents; fragrances; buffers; dispersants; conditioning agents; film-forming agents; ceramides; preserving agents; stabilizers; and opacifiers.

32. A composition according to claim 1, comprising at least one oxidizing agent.

33. A composition according to claim 32, wherein the at least one oxidizing agent is chosen from hydrogen peroxide, urea peroxide, alkali metal bromates, persalts, and enzymes.

34. A process for treating keratin fibers, wherein a composition comprising, in a cosmetically acceptable medium comprising water or a mixture of water and at least one organic solvent, at least one direct dye that is soluble in said medium, of formula (I) or (I'):

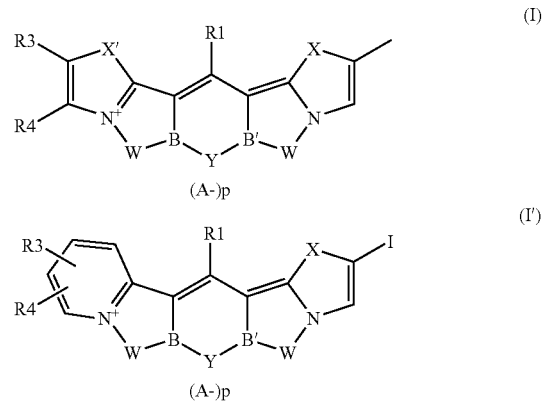

wherein:
R1 is chosen from:
  hydrogen atoms,
  linear, branched or cyclic alkyl radicals comprising from 1 to 22 carbon atoms, optionally substituted with at least one group chosen from
    hydroxyl,
    linear or branched $C_1$-$C_6$ alkoxy,
    $C_1$-$C_6$ cycloalkoxy, and
    phenyl, optionally substituted with at least one carboxyl group,
  $C_6$-$C_{30}$ aryl radicals, and
  amino radicals substituted with at least one radical chosen from linear or branched $C_1$-$C_6$ alkyls or hydroxyalkyls;
R3, R4, R5 and R6, which may be identical or different, are each chosen from:
  hydrogen atoms;
  linear or branched alkyl radicals comprising from 1 to 22 carbon atoms, optionally substituted with at least one hydroxyl radicals;
  halogen atoms,
  carboxyl radicals, and
  sulfo radicals;
or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle;

wherein each aliphatic or aromatic ring or heterocycle are optionally substituted with at least one substituent chosen from:
- halogen atoms,
- $C_1$-$C_6$ alkoxy radicals,
- carboxyl radicals,
- sulfo radicals and
- $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group, B and B', which may be identical or different, are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, ($C_6$-$C_{30}$)aryloxy($C_1$-$C_6$) alkyls or ($C_1$-$C_4$)alkyl ($C_6$-$C_{30}$)arylaminos;

X and X', which may be identical or different, are each chosen from O, S, N, NR'7, Se and CR'8R'9;

Y is chosen from O, S, N, Se, NR7, CO and CR8R9;

R8 and R9, which may be identical or different, are each chosen from
- hydrogen atoms; and
- linear or branched $C_1$-$C_{22}$ alkyl radicals optionally substituted with at least one group chosen from
  - hydroxyls,
  - $C_1$-$C_{10}$ mono- or dialkylaminos,
  - $C_1$-$C_{10}$ mono- or dihydroxyalkylaminos,
  - $C_{10}$-$C_{30}$ aryls,
  - $C_{10}$-$C_{30}$ aryloxys and
  - ($C_2$-$C_{10}$)acylaminos;

R7 is chosen from
- hydrogen atoms,
- linear or branched $C_1$-$C_{10}$ alkyl radicals,
- $C_6$-$C_{30}$ aryl radicals,
- amino radicals bearing at least one $C_6$-$C_{30}$ aryl radical optionally substituted with at least one substituent chosen from
  - $C_1$-$C_6$ alkyl radicals
  - carboxyl radicals,
  - ($C_1$-$C_4$)alkyl($C_6$-$C_{30}$)arylsulfonyl radicals,
  - $C_2$-$C_{10}$ acyl radicals,
  - tri($C_1$-$C_4$)alkylamino($C_1$-$C_4$)alkylcarbonyl radicals, and
  - aminothiocarbonyl groups;

Z and
N=Z,
wherein Z is chosen from an optionally fused 5- or 6-membered heterocycle comprising from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and ($C_1$-$C_4$)alkoxycarbonyl($C_1$-$C_6$)alkyl radicals;

p is an number ranging from 0 to 1; and $A^-$ is chosen from organic anions and mineral anions, or a mixture of anions, is applied to said wet or dry fibers, for a time that is sufficient to develop the coloration, after which the fibers are rinsed, optionally washed with shampoo, rinsed again and dried, or the resulting fibers are left to dry.

35. A process for treating keratin fibers wherein a composition comprising, in a cosmetically acceptable medium comprising water or a mixture of water and at least one organic solvent, at least one direct dye that is soluble in said medium, of formula (I) or (I'):

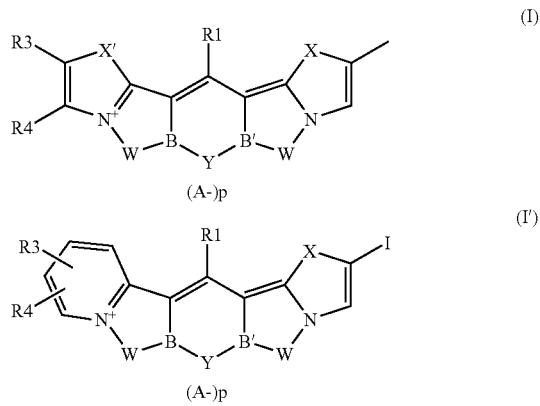

wherein:
R1 is chosen from:
- hydrogen atoms,
- linear, branched or cyclic alkyl radicals comprising from 1 to 22 carbon atoms, optionally substituted with at least one group chosen from
  - hydroxyl,
  - linear or branched $C_1$-$C_6$ alkoxy,
  - $C_1$-$C_6$ cycloalkoxy, and
  - phenyl, optionally substituted with at least one carboxyl group,
- $C_6$-$C_{30}$ aryl radicals, and
- amino radicals substituted with at least one radical chosen from linear or branched $C_1$-$C_6$ alkyls or hydroxyalkyls;

R3, R4, R5 and R6, which may be identical or different, are each chosen from:
- hydrogen atoms;
- linear or branched alkyl radicals comprising from 1 to 22 carbon atoms, optionally substituted with at least one hydroxyl radicals;
- halogen atoms,
- carboxyl radicals, and
- sulfo radicals;

or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle; wherein each aliphatic or aromatic ring or heterocycle are optionally substituted with at least one substituent chosen from:
- halogen atoms,
- $C_1$-$C_6$ alkoxy radicals,
- carboxyl radicals,
- sulfo radicals and
- $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group, B and B', which may be identical or different are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, $(C_6$-$C_{30})$aryloxy$(C_1$-$C_6)$ alkyls or $(C_1$-$C_4)$alkyl $(C_6C_{30})$arylaminos;

X and X', which may be identical or different, are each chosen from O, S, N, NR'7, Se and CR'8R'9;

Y is chosen from O, S, N, Se, NR7, CO and CR8R9;

R8 and R9, which may be identical or different, are each chosen from hydrogen atoms; and linear or branched $C_1$-$C_{22}$ alkyl radicals optionally substituted with at least one group chosen from hydroxyls, $C_1$-$C_{10}$ mono- or dialkylaminos, $C_1$-$C_{10}$ mono- or dihydroxyalkylaminos, $C_{10}$-$C_{30}$ aryls, $C_{10}$-$C_{30}$ aryloxys and $(C_2$-$C_{10})$acylaminos;

R7 is chosen from hydrogen atoms, linear or branched $C_1$-$C_{10}$ alkyl radicals, $C_6$-$C_{30}$ aryl radicals, amino radicals bearing at least one $C_6$-$C_{30}$ aryl radical optionally substituted with at least one substituent chosen from $C_1$-$C_6$ alkyl radicals carboxyl radicals, $(C_1$-$C_4)$alkyl$(C_6$-$C_{30})$arylsulfonyl radicals, $C_2$-$C_{10}$ acyl radicals, tri$(C_1$-$C_4)$alkylamino$(C_1$-$C_4)$alkylcarbonyl radicals, and aminothiocarbonyl groups;

Z and

N=Z, wherein Z is chosen from an optionally fused 5- or 6-membered heterocycle comprising from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and $(C_1$-$C_4)$alkoxycarbonyl$(C_1$-$C_6)$alkyl radicals;

p is an number ranging from 0 to 1; and

A⁻ is chosen from organic anions and mineral anions, or a mixture of anions, is applied to said wet or dry fibers without final rinsing.

36. A multi-compartment device for dyeing and lightening the hair, comprising at least one compartment comprising a composition comprising, in a cosmetically acceptable medium comprising water or a mixture of water and at least one organic solvent, at least one direct dye that is soluble in said medium, of formula (I) or (I'):

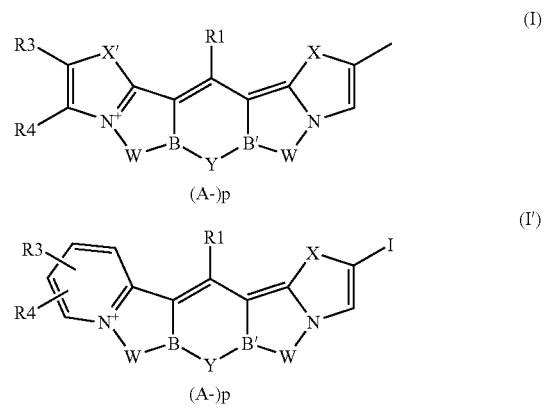

wherein:

R1 is chosen from:

hydrogen atoms, linear, branched or cyclic alkyl radicals comprising from 1 to 22 carbon atoms, optionally substituted with at least one group chosen from hydroxyl, linear or branched $C_1$-$C_6$ alkoxy, $C_1$-$C_6$ cycloalkoxy, and phenyl, optionally substituted with at least one carboxyl group, $C_6$-$C_{30}$ aryl radicals, and amino radicals substituted with at least one radical chosen from linear or branched $C_1$-$C_6$ alkyls or hydroxyalkyls;

R3, R4, R5 and R6, which may be identical or different, are each chosen from:

hydrogen atoms;

linear or branched alkyl radicals comprising from 1 to 22 carbon atoms, optionally substituted with at least one hydroxyl radicals;

halogen atoms, carboxyl radicals, and sulfo radicals;

or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle; wherein each aliphatic or aromatic ring or heterocycle are optionally substituted with at least one substituent chosen from:

halogen atoms, $C_1$-$C_6$ alkoxy radicals, carboxyl radicals, sulfo radicals and $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group, B and B', which may be identical or different, are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, $(C_6$-$C_{30})$aryloxy$(C_1$-$C_6)$ alkyls or $(C_1$-$C_4)$alkyl $(C_6$-$C_{30})$arylaminos;

X and X', which may be identical or different, are each chosen from O, S, N, NR'7, Se and CR'8R'9;

Y is chosen from O, S, N, Se, NR7, CO and CR8R9;

R8 and R9, which may be identical or different, are each chosen from hydrogen atoms;

linear or branched $C_1$-$C_{22}$ alkyl radicals optionally substituted with at least one group chosen from hydroxyls, $C_1$-$C_{10}$ mono- or dialkylaminos, $C_1$-$C_{10}$ mono- or dihydroxyalkylaminos, $C_{10}$-$C_{30}$ aryls, $C_{10}$-$C_{30}$ aryloxys and $(C_2$-$C_{10})$acylaminos;

R7 is chosen from hydrogen atoms, linear or branched $C_1$-$C_{10}$ alkyl radicals, $C_6$-$C_{30}$ aryl radicals, amino radicals bearing at least one $C_6$-$C_{30}$ aryl radical optionally substituted with at least one substituent chosen from $C_1$-$C_6$ alkyl radicals carboxyl radicals, $(C_1$-$C_4)$alkyl$(C_6$-$C_{30})$arylsulfonyl radicals, $C_2$-$C_{10}$ acyl radicals, tri$(C_1$-$C_4)$alkylamino$(C_1$-$C_4)$alkylcarbonyl radicals, and aminothiocarbonyl groups;

Z and

N=Z, wherein Z is chosen from an optionally fused 5- or 6-membered heterocycle comprising from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and $(C_1$-$C_4)$alkoxycarbonyl$(C_1$-$C_6)$alkyl radicals;

p is an number ranging from 0 to 1; and $A^-$ is chosen from organic anions and mineral anions, or a mixture of anions, and at least one other compartment comprising a composition comprising at least one oxidizing agent.

37. A process for dyeing keratin materials comprising applying to said fibers at least one composition comprising, in a cosmetically acceptable medium comprising water or a mixture of water and at least one organic solvent, at least one direct dye that is soluble in said medium, of formula (I) or (I'):

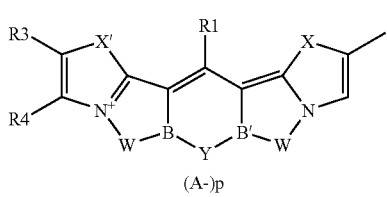

(I)

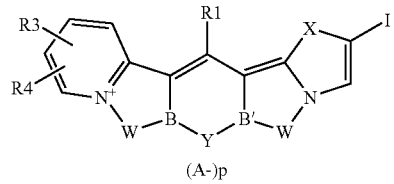

(I')

wherein:

R1 is chosen from:

hydrogen atoms, linear, branched or cyclic alkyl radicals comprising from 1 to 22 carbon atoms, optionally substituted with at least one group chosen from hydroxyl, linear or branched $C_1$-$C_6$ alkoxy, $C_1$-$C_6$ cycloalkoxy, and phenyl, optionally substituted with at least one carboxyl group, $C_6$-$C_{30}$ aryl radicals, and amino radicals substituted with at least one radical chosen from linear or branched $C_1$-$C_6$ alkyls or hydroxyalkyls;

R3, R4, R5 and R6, which may be identical or different, are each chosen from:

hydrogen atoms;

linear or branched alkyl radicals comprising from 1 to 22 carbon atoms, optionally substituted with at least one hydroxyl radicals;

halogen atoms, carboxyl radicals, and sulfo radicals;

or R3 and R4 and/or R5 and R6 together with the carbon atoms to which each is attached, form 6- to 30-membered aliphatic or aromatic rings or heterocycles, optionally fused to an identical or different 6- to 30-membered aromatic ring or heterocycle; wherein each aliphatic or aromatic ring or heterocycle are optionally substituted with at least one substituent chosen from:

halogen atoms, $C_1$-$C_6$ alkoxy radicals, carboxyl radicals, sulfo radicals and $C_6$-$C_{30}$ aryl radicals with at least one linear or branched $C_1$-$C_6$ alkyl radical optionally interrupted with an aminocarbonyl or carbonylamino group and optionally ending with a hydroxyl, carboxyl, amino or hydrogenocarbonylamino group, B and B', which may be identical or different, are each chosen from nitrogen atoms or CH groups;

W is chosen from a divalent radical comprising two carbon atoms, such that the sequence N—W—B does or does not comprise an unsaturation, said divalent radical is optionally substituted with a group chosen from $C_1$-$C_6$ alkyls, $(C_6$-$C_{30})$aryloxy$(C_1$-$C_6)$ alkyls or $(C_1$-$C_4)$alkyl$(C_6$-$C_{30})$arylaminos;

X and X', which may be identical or different, are each chosen from O, S, N, NR'7, Se and CR'8R'9;

Y is chosen from O, S, N, Se, NR 7, CO and CR8R9;

R8 and R9, which may be identical or different, are each chosen from
- hydrogen atoms; and
- linear or branched $C_1$-$C_{22}$ alkyl radicals optionally substituted with at least one group chosen from
  - hydroxyls,
  - $C_1$-$C_{10}$ mono- or dialkylaminos,
  - $C_1$-$C_{10}$ mono- or dihydroxyalkylaminos,
  - $C_{10}$-$C_{30}$ aryls,
  - $C_{10}$-$C_{30}$ aryloxys and
  - ($C_2$-$C_{10}$)acylaminos;

R7 is chosen from
- hydrogen atoms,
- linear or branched $C_1$-$C_{10}$ alkyl radicals,
- $C_6$-$C_{30}$ aryl radicals,
- amino radicals bearing at least one $C_6$-$C_{30}$ aryl radical optionally substituted with at least one substituent chosen from
  - $C_1$-$C_6$ alkyl radicals
  - carboxyl radicals,
  - ($C_1$-$C_4$)alkyl($C_6$-$C_{30}$)arylsulfonyl radicals,
  - $C_2$-$C_{10}$ acyl radicals,
  - tri($C_1$-$C_4$)alkylamino($C_1$-$C_4$)alkylcarbonyl radicals, and
  - aminothiocarbonyl groups;
- Z and
- N=Z, wherein Z is chosen from an optionally fused 5- or 6-membered heterocycle comprising from 1 to 30 carbon atoms, wherein at least one of the carbon atoms is optionally replaced with a CO group;

R'7 is chosen from hydrogen atoms, $C_1$-$C_6$ alkyl radicals and $C_1$-$C_6$ hydroxyalkyl radicals;

R'8 and R'9, which may be identical or different, are each chosen from hydrogen atoms, $C_1$-$C_6$ alkyl radicals, $C_1$-$C_6$ hydroxyalkyl radicals, $C_1$-$C_6$ carboxyalkyl radicals and ($C_1$-$C_4$)alkoxycarbonyl($C_1$-$C_6$)alkyl radicals;

p is an number ranging from 0 to 1; and $A^-$ is chosen from organic anions and mineral anions, or a mixture of anions.

* * * * *

UNITED STATES PATENT AND TRADEMARK OFFICE
CERTIFICATE OF CORRECTION

PATENT NO.         : 7,427,301 B2                                Page 1 of 2
APPLICATION NO. : 11/223962
DATED              : September 23, 2008
INVENTOR(S)        : Alain Lagrange It is certified that error appears in the above-identified patent and that said Letters Patent is hereby corrected as shown below:

In claim 1, col. 60, lines 15-30;
In claim 34, col. 66, lines 20-35;
In claim 35, col. 68, lines 10-25;
In claim 36, col. 70, lines 5-20; and
In claim 37, col. 71, lines 60-65- col. 72, lines 1-10, "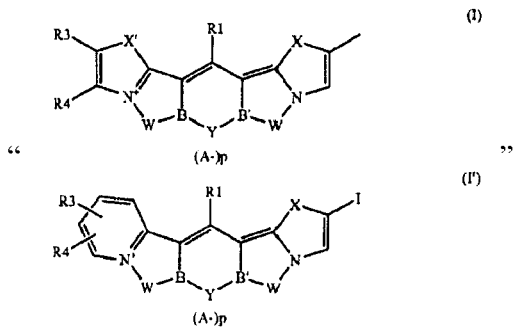"

should read:

--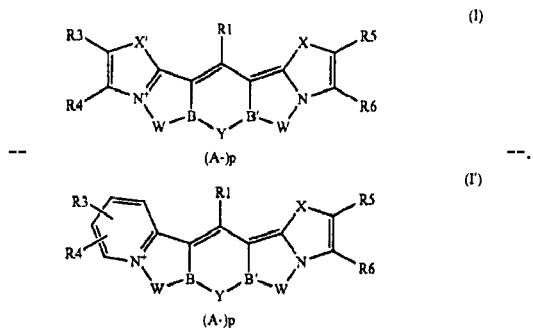--.

UNITED STATES PATENT AND TRADEMARK OFFICE
CERTIFICATE OF CORRECTION

PATENT NO. : 7,427,301 B2
APPLICATION NO. : 11/223962
DATED : September 23, 2008
INVENTOR(S) : Alain Lagrange It is certified that error appears in the above-identified patent and that said Letters Patent is hereby corrected as shown below:

In claim 11, col. 62, line 38,
"ethyl-6,7,7*a*8,8*a*,9,10,16-octahydro8-[(4-methylphe-"

should read
-- ethyl-6,7,7*a*8,8*a*,9,10,16-octahydro-8-[(4-methylphe- --.

In claim 11, col. 63, line 12,
"[4,3-b]naphthyridin-5-ium, 8-(2-benzothiazoly-"

should read
-- [4,3-b][1,6]naphthyridin-5-ium, 8-(2-benzothiazoly- --.

Signed and Sealed this

Eighteenth Day of November, 2008

JON W. DUDAS
*Director of the United States Patent and Trademark Office*